US006569630B1

(12) United States Patent
Vivekananda et al.

(10) Patent No.: US 6,569,630 B1
(45) Date of Patent: May 27, 2003

(54) METHODS AND COMPOSITIONS FOR APTAMERS AGAINST ANTHRAX

(75) Inventors: Jeevalatha Vivekananda, San Antonio, TX (US); Johnathan L. Kiel, Universal City, TX (US)

(73) Assignee: Conceptual MindWorks, Inc., San Antonio, TX (US)

( * ) Notice: Subject to any disclaimer, the term of this patent is extended or adjusted under 35 U.S.C. 154(b) by 0 days.

(21) Appl. No.: 09/978,753

(22) Filed: Oct. 15, 2001

Related U.S. Application Data

(63) Continuation-in-part of application No. 09/909,492, filed on Jul. 19, 2001, now abandoned, which is a continuation-in-part of application No. 09/608,706, filed on Jun. 30, 2000, now Pat. No. 6,303,316.
(60) Provisional application No. 60/291,371, filed on May 15, 2001, provisional application No. 60/199,620, filed on Apr. 25, 2000, and provisional application No. 60/142,301, filed on Jul. 2, 1999.

(51) Int. Cl.[7] .............................. C12Q 1/68; C12P 19/34; C07H 21/04; C07H 21/02

(52) U.S. Cl. .................. 435/6; 435/91.2; 536/22.1; 536/23.1
(58) Field of Search ................ 435/6, 91.2; 536/22.1, 536/23.1, 25.4

(56) References Cited

U.S. PATENT DOCUMENTS 6,303,316 B1 * 10/2001 Kiel et al. ..................... 435/6

FOREIGN PATENT DOCUMENTS

WO        WO 01/006249        *  1/2001

* cited by examiner

*Primary Examiner*—Stephanie W. Zitomer
(74) *Attorney, Agent, or Firm*—Richard A. Nakashima; Blakely, Sokoloff, Taylor & Zafman

(57) ABSTRACT

The present invention concerns methods of preparing nucleic acid ligands against anthrax spores, compositions comprising anthrax specific nucleic acid ligands and methods of use of such ligands for detection and/or neutralization of anthrax spores.

13 Claims, 5 Drawing Sheets

CONTROL SPORE

HPM EXPOSED WITH DALM

METHODS AND COMPOSITIONS FOR APTAMERS AGAINST ANTHRAX

This application is a continuation-in-part of U.S. patent application Ser. No. 09/909,492, filed Jul. 19, 2001 now abandoned, which was a continuation-in-part of U.S. patent application Ser. No. 09/608,706, filed Jun. 30, 2000 (now issued U.S. Pat. No. 6,303,316), which claimed the benefit under 35 U.S.C. §119(e) of provisional Patent Application Serial No. 60/142,301, filed Jul. 2, 1999 and No. 60/199,620, filed Apr. 25, 2000. This application claims the benefit under 35 U.S.C. §119(e) of provisional Patent Application Serial No. 60/291,371, filed May 15, 2001, the entire text of which is incorporated herein by reference.

STATEMENT REGARDING FEDERALLY SPONSORED RESEARCH OR DEVELOPMENT

The Federal Government has rights to use the present invention pursuant to contract F41624-00-D-7000 awarded by the Department of the Air Force.

BACKGROUND OF THE INVENTION

1. Field of the Invention

The present invention relates to the field of detection of biological agents using novel compositions, methods and apparatus comprising one or more nucleic acid ligands operably coupled to an organic semiconductor. More particularly, the present invention relates to the production and use of nucleic acid ligands against anthrax spores.

2. Description of Related Art

There is a great need for the development of methods, compositions and apparatus capable of detecting and identifying known or unknown chemical and biological agents (herein referred to as analytes), which include but are not limited to nucleic acids, proteins, illicit drugs, explosives, toxins, pharmaceuticals, carcinogens, poisons, allergens, contaminants, pathogens and infectious agents.

As one skilled in the art will readily appreciate, any method, technique or device capable of such detection and identification would have numerous medical, industrial forensic and military applications. For instance, such methods, techniques and devices could be employed in the diagnosis and treatment of disease, to develop new compounds for pharmaceutical, medical or industrial purposes, or to identify chemical and biological warfare agents.

Current methods, techniques and devices that have been applied to identification of chemical and biological analytes typically involve capturing the analyte through the use of a non-specific solid surface or through capture deoxyribonucleic acids (DNA) or antibodies. A number of known binding agents must then be applied, particularly in the case of biological analytes, until a binding agent with a high degree of affinity for the analyte is identified. A labeled antiligand (e.g., labeled DNA or labeled antibodies) must be applied, where the antiligand causes, for example, the color or fluorescence of the analyte to change if the binding agent exhibits affinity for the analyte (i.e., the binding agent binds with the analyte). The analyte may be identified by studying which of the various binding agents exhibited the greatest degree of affinity for the analyte.

There are a number of problems associated with current methods of chemical and biological agent identification. It takes a great deal of time and effort to repetitiously apply each of the known labeled antiligands, until an antiligand exhibiting a high degree of affinity is found. Accordingly, these techniques are not conducive to easy automation. Current methods are also not sufficiently robust to work in the heat, dust, humidity or other environmental conditions that might be encountered, for example, on a battlefield or in a food processing plant. Portability and ease of use are also problems seen with current methods for chemical and biological agent identification.

Within the field of biological warfare, there is a great need for a rapid, sensitive method to detect and identify pathogenic spores of Bacillus anthrax (hereafter "anthrax"). Anthrax is a highly pathogenic biological agent that is relatively simple to produce and distribute in the field. Present methods for detection of anthrax are not sufficiently rapid, sensitive, and robust to allow early detection of exposure to anthrax under field conditions, such as might be encountered on a battlefield. No good method presently exists for neutralization of anthrax under field conditions.

SUMMARY OF THE INVENTION

The present invention fulfills an unresolved need in the art, by providing methods, compositions and apparatus for the production of nucleic acid ligands capable of binding to, identifying and/or neutralizing anthrax. The methods and compositions disclosed herein provide substantial improvements over earlier methods for anthrax detection (e.g., Reif et al., 1994; Gatto-Menking et al., 1995; Bruno and Yu, 1996), by utilizing anthrax-binding nucleic acid ligands.

The compositions of the present invention comprise a recognition complex or a recognition complex system that are capable of detecting, identifying, characterizing or purifying a chemical or biological agent (hereafter, "analyte"), preparing or purifying high affinity nucleic acid ligands for selected known analytes, using high affinity nucleic acid ligands to measure the concentration of analyte in a sample or to neutralize an analyte, or to perform high through-put screening of libraries of compounds or native plant extracts for compounds that are structural analogs of known inhibitors, activators or binding agents of bioactive molecules. The recognition complex and recognition complex system and the corresponding techniques should be capable of full automation.

Each recognition complex is comprised of a nucleic acid ligand operably coupled to an organic semiconductor. In certain embodiments, the organic semiconductor is DALM (diazoluminomelanin), although the use of other organic semiconductors, such as polyphenylenes, is contemplated within the scope of the invention. In various embodiments, the organic semiconductor may be attached to the nucleic acid ligand by either covalent or non-covalent interaction.

In preferred embodiments, the nucleic acid ligand is DNA, although it is contemplated within the scope of the invention that other nucleic acids comprised of RNA or synthetic nucleotide analogs could be utilized as well. In certain embodiments, the nucleic acid ligand sequences are random, or may be generated from libraries of random DNA sequences. In other embodiments, the nucleic acid ligand sequences may not be random, but may rather be designed to react with specific target analytes. In a preferred embodiment, the nucleic acid ligand sequences are aptamers (Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823 and PCT application WO 99/31275, each incorporated herein by reference).

In certain embodiments, the analyte to be identified may be added in the form of a complex mixture that may include, for example, aqueous or organic solvent, proteins, lipids, nucleic acids, detergents, particulates, intact cells, bacteria, viruses and spores, as well as other components. In other embodiments, the analyte may be partially or fully purified before exposure to the array. In particularly preferred embodiments, the analyte is anthrax spore.

In certain embodiments, a recognition complex system, comprising two or more recognition complexes, may be used in methods for identifying an analyte. After the analyte is contacted with the recognition complexes, certain recognition complexes will bind the analyte, while others will not. Binding of analyte to a recognition complex may be detected by changes in the electrochemical properties of the nucleic acid ligand/organic semiconductor couplet upon binding to the analyte. Nonlimiting examples of electrochemical signals include photochemical, fluorescent or luminescent signals, changes in color or changes in electrical conductivity. The degree to which the electrochemical properties change is a function of the degree to which the nucleic acid ligand binds the analyte. Accordingly, the electrochemical changes that occur across all of the recognition complexes, when taken as a whole, can be used as a unique signature to identify the analyte.

To facilitate detection of such electrochemical changes, the recognition complex system may be associated with a detection unit operably coupled to the recognition complexes. Non-limiting examples of detection units include a charge coupled device (CCD), a CCD camera, a photomultiplier tube, a spectrophotometer or a fluorometer. The recognition complex system may also be associated with system memory for storing electrochemical signals, as well as a data processing unit that may comprise a neural network or lookup tables. For embodiments where the binding of analyte is detected by changes in electrical conductivity of the recognition complex, the complexes may be positioned between a pair of electrodes attached to a conductivity meter.

In addition to analyte identification, recognition complexes may be used to screen for the presence or measure the amount of analytes that are biological molecules, such as hormones, cytokines, vitamins, metabolites or other compounds, in samples of human tissue, fluids or extracts. Nucleic acid ligands with high affinity for biological molecules of interest may be prepared as described below. Upon exposure of recognition complexes incorporating the high affinity ligands to a sample, the presence of the biological molecule is indicated by its binding to the ligand. Since binding of analyte to ligand results in an electrochemical signal, the concentration of biological molecule in the sample can be readily determined by quantifying the signal. Where the biological molecule of interest is part of a macromolecular complex, flow cytometry may also be used to detect and quantify the amount of biological molecule in a sample.

In certain embodiments, the recognition complex system may be used to enrich or purify analytes that bind to one or more selected nucleic acid ligands. In a preferred embodiment, selected nucleic acid ligands are attached to a surface and exposed to a population of analytes. After binding of analyte to nucleic acid ligand, the unbound analytes are removed and the enriched or purified bound analyte is eluted from the ligand. Enrichment and purification may occur using either an interative process, with multiple cycles of binding, separation and elution, or by a single-step process. Separation of bound from unbound analyte may occur by any method known in the art. In a non-limiting example, the ligands may be attached to a column chromatography resin or other solid support and exposed to a mixture of analytes. Unbound analyte may be removed by simple washing of the column or other support. Bound analyte may be eluted by exposure to solutions containing appropriate salt concentration, pH, detergent content, chaotrophic agent or other substance that interferes with the binding interaction. Depending on the affinity of analyte for ligand and the stringency of the initial binding interaction, it may be possible to obtain a relatively purified analyte with a single binding step.

In certain embodiments, the recognition complexes may be attached to a surface, such as a Langmuir-Blodgett film, functionalized glass, germanium, silicon, PTFE, polystyrene, gallium arsenide, gold, silver, membrane, nylon, glass bead, magnetic bead or PVP. In preferred embodiments, the recognition complex system of the present invention employs organic semiconductor chip technology wherein nucleic acid ligands are distributed across the surface of the chip so as to form an array of recognition complexes. In other embodiments, the recognition complexes of the present invention may be attached to a surface for use in a flow cell apparatus.

In additional embodiments, the nucleic acid ligands are attached to magnetic beads instead of to a chip. An array of nucleic acid ligands may be assembled, each attached to a magnetic bead. In certain embodiments, each nucleic acid ligand attached to a single magnetic bead has the same nucleic acid sequence, while in other embodiments a single magnetic bead may be attached to nucleic acid ligands of different sequences. In a preferred embodiment, the magnetic bead is attached to an organic semiconductor, such as DALM, and the nucleic acid ligand is attached to the organic semiconductor, forming an array of recognition complexes. Although any method may be employed within the scope of the present invention to attach the organic semiconductor to the magnetic bead and the nucleic acid ligand to the organic semiconductor, in a preferred embodiment the organic semiconductor is covalently attached to the magnetic bead and the nucleic acid ligand is non-covalently attached to the organic semiconductor. In a more preferred embodiment, the attachment of nucleic acid ligand to organic semiconductor is an electrostatic interaction, preferably mediated by magnesium ion.

In certain embodiments, an array of recognition complexes attached to magnetic beads is exposed to an analyte and binding of analyte to nucleic acid ligand may be detected, for example, by photochemical changes in the nucleic acid ligand/DALM couplet upon binding to the analyte. The skilled artisan will realize that magnetic beads would be particularly useful for separating recognition complexes that bind to the analyte from recognition complexes that do not bind the analyte. In one embodiment, a magnetic flow cell, such as is described in U.S. Pat. No. 5,972,721 (incorporated herein by reference), could be used in conjunction with the recognition complex system to identify and separate analyte-binding recognition complexes from recognition complexes that do not bind the analyte.

In certain preferred embodiments, flow cytometry is used to separate recognition complexes that bind to an analyte from those that do not bind. In such embodiments, the recognition complex may be attached to a glass or other bead, or the analyte may comprise a population of cells, spores or other large particles for analytical or preparative procedures. Nucleic acid ligands that bind to the target analyte, or analytes that bind to a specific nucleic acid ligand, may be sorted, for example, by screening particles for DALM-associated fluorescence in a flow cytometer.

In certain embodiments, the recognition complex system may be subject to an iterative process to increase the specificity and affinity of the nucleic acid ligands for an analyte of interest. In such embodiments, nucleic acid ligand sequences that bind a selected analyte are identified, separated, amplified (e.g., using a polymerase chain reaction) and attached to organic semiconductor to form a new recognition complex system. The nucleic acid ligand sequences that do not bind to the analyte are discarded. The new recognition complex system is exposed to the analyte and binding of analyte to nucleic acid ligands produces an enhanced electrochemical signature, as the nucleic acid ligand sequences present will more specifically compliment the analyte. This procedure may be repeated, with each iteration producing a more unique or enhanced signature.

In a further embodiment, this iterative process may be used to identify and amplify one or more nucleic acid ligand sequences that exhibit the highest degree of affinity for a specific analyte. Production of a nucleic acid ligand that binds to the analyte with high affinity (dissociation constant of 1.0 $\mu$M or lower) would have utility in a variety of applications. For certain embodiments, production of a nucleic acid ligand with a dissociation constant of 100 nM or lower, more preferably 10 nM or lower, most preferably 1 nM or lower is preferred. This process also provides a method for purifying a nucleic acid ligand that binds to a target analyte. Purification may be less than 100%, the only requirement being that the nucleic acid ligand of interest is present in significantly greater proportion in the final mixture compared to the starting material. A "purified" nucleic acid ligand may comprise 10% or more, preferably 20% or more, more preferably 40% or more, more preferably 60% or more, more preferably 80% or more, more preferably 95% or more of the total nucleic acid content of the "purified" fraction.

It is contemplated within the scope of the present invention that separation of bound from unbound nucleic acid ligands may occur using virtually any method that can separate bound from unbound ligands. Non-limiting examples include use of nucleic acid chips, use of magnetic beads and magnetic filters, use of glass or other beads and flow cytometry, and flow cytometry using cells as the target analyte. In any case, further iterations of the binding and separation steps will result in progressive enrichment (purification) of ligands that bind to the analyte. If desired, the stringency of the binding interaction may be increased, for example by increasing the temperature or by raising or lowering the salt concentration or the pH of the solution.

In another embodiment, nucleic acid ligands that bind to the analyte with high affinity can be reproduced (synthesized or amplified) for use as a neutralizing agent to inactivate or destroy the analyte. A high affinity nucleic acid ligand may be attached to a variety of agents that could be used to neutralize the analyte, such as toxic proteins, enzymes capable of activating protoxins, or other molecules or reactive moieties including radioisotopes and other organic or inorganic compounds. In certain embodiments, the high affinity nucleic acid ligand can be attached to an organic semiconductor, such as DALM. The DALM/nucleic acid ligand couplet, after binding to the analyte, may be activated by a variety of techniques, including exposure to sunlight, heat, or irradiation of various types, including laser, microwave, radiofrequency, ultraviolet and infrared. Activation of the DALM/nucleic acid ligand couplet results in absorption of energy, which may be transmitted to the analyte, inactivating or destroying it. See U.S. Pat. No. 6,303,316, incorporated herein by reference.

In certain embodiments, the high affinity nucleic acid ligand could be incorporated into an apparatus capable of being carried into the field. For example, the high affinity nucleic acid ligand could be incorporated into a patch or card to be worn by an individual. Exposure of the individual to the specific analyte for which the nucleic acid ligand exhibits high affinity could be indicated by a color change of the patch, or by a change in the electrical or photochemical properties of a nucleic acid ligand/organic semiconductor couplet. Alternatively, the high affinity nucleic acid ligand could be incorporated into an apparatus to be carried by a vehicle that could be used to cover a wide area to detect and identify unknown chemical or biological agents.

The skilled artisan will realize that the scope of the present invention is not limited to applications in chemical or biological warfare, but rather includes a broad variety of potential applications in industry and medicine, where early detection and identification of exposure to chemical or biological agents is desired. Non-limiting examples of such applications include to detect explosives or illegal drugs in an airport detection system, to detect air-borne pathogens in an air conditioner monitoring system, to detect water-borne pathogens, carcinogens, teratogens or toxins in a water quality monitoring system, to detect pathogens in a hospital operating room monitoring system, to screen for pathogens in samples of human tissues or fluids, to detect allergens, pathogens or contaminants in a food production monitoring system, to detect genetically modified organisms, or to perform high through-put screening for pharmaceutical compounds.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

Figure 1:
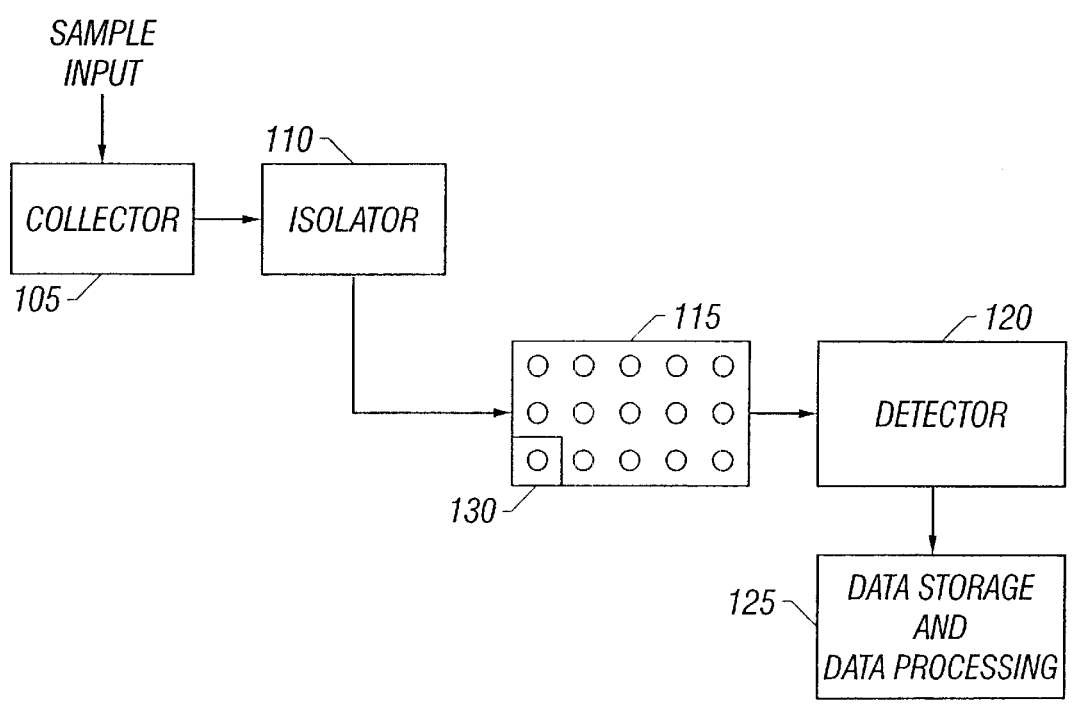
FIG. 1 illustrates a recognition complex system in accordance an exemplary embodiment of the present invention.

As used herein, "a" or "an" may mean one or more than one of an item.

"Nucleic acid" means either DNA, RNA, single-stranded, double-stranded or triple stranded and any chemical modifications thereof. Virtually any modification of the nucleic acid is contemplated by this invention. Non-limiting examples of nucleic acid modifications are discussed in further detail below. "Nucleic acid" encompasses, but is not limited to, oligonucleotides and polynucleotides. "Oligonucleotide" refers to at least one molecule of between about 3 and about 100 nucleotides in length. "Polynucleotide" refers to at least one molecule of greater than about 100 nucleotides in length. These terms generally refer to at least one single-stranded molecule, but in certain embodiments also encompass at least one additional strand that is partially, substantially or fully complementary in sequence. Thus, a nucleic acid may encompass at least one double-stranded molecule or at least one triple-stranded molecule that comprises one or more complementary strand(s) or "complement (s)." As used herein, a single stranded nucleic acid may be denoted by the prefix "ss", a double stranded nucleic acid by the prefix "ds", and a triple stranded nucleic acid by the prefix "ts."

Within the practice of the present invention, a "nucleic acid" may be of almost any length, from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10000, 15000, 20000 or even more bases in length. The term "nucleic acid" will generally refer to at least one molecule or strand of DNA, RNA or a derivative or mimic thereof, comprising at least one nucleobase. A "nucleobase" refers to a heterocyclic base, for example, a purine or pyrimidine base naturally found in DNA (e.g. adenine "A," guanine "G," thymine "T" and cytosine "C") or RNA (e.g. A, G, uracil "U" and C), as well as their derivatives and mimics. A "derivative" refers to a chemically modified or altered form of a naturally occurring molecule, while "mimic" and "analog" refer to a molecule that may or may not structurally resemble a naturally occurring molecule, but that functions similarly to the naturally occurring molecule.

As used herein, a "moiety" generally refers to a smaller chemical or molecular component of a larger chemical or molecular structure.

A "nucleoside" is an individual chemical unit comprising a nucleobase covalently attached to a nucleobase linker moiety. An example of a "nucleobase linker moiety" is a sugar comprising 5-carbon atoms (a "5-carbon sugar"), including but not limited to deoxyribose, ribose or arabinose, and derivatives or mimics of 5-carbon sugars. Examples of derivatives or mimics of 5-carbon sugars include 2'-fluoro-2'-deoxyribose or carbocyclic sugars where a carbon is substituted for the oxygen atom in the sugar ring.

A "nucleotide" refers to a nucleoside further comprising a "backbone moiety" used for the covalent attachment of one or more nucleotides to another molecule or to each other to form a nucleic acid. The "backbone moiety" in naturally occurring nucleotides typically comprises a phosphorus moiety covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety.

"Nucleic acid ligand" means a non-naturally occurring nucleic acid having a desirable action on a target. A desirable action includes, but is not limited to, binding of the target, catalytically changing the target, reacting with the target in a way that modifies or alters the target or the functional activity of the target, covalently attaching to the target, facilitating the reaction between the target and another molecule, and neutralizing the target. In a preferred embodiment, the action is specific binding affinity for a target molecule, such target molecule being a three dimensional chemical structure. The meaning of "nucleic acid ligand" specifically excludes nucleic acids that bind to another nucleic acid through a mechanism which predominantly depends on Watson/Crick base pairing. Nucleic acid ligands include, but are not limited to, nucleic acids that are identified by the SELEX process discussed below.

"SELEX" (Systematic Evolution of Ligands by Exponential enrichment) involves the combination of selection of nucleic acid ligands which interact with a target in a desirable manner, for example binding to the target, with amplification of those selected nucleic acid ligands. Iterative cycling of the selection/amplification steps allows selection of one or a small number of nucleic acid ligands that interact most strongly with the target from a pool that contains a very large number of nucleic acid ligands. Cycling of the selection/amplification procedure is continued until a selected goal is achieved. In certain embodiments of the present invention, the goal may be to produce one or more nucleic acid ligands that, for example, can be used to bind to and detect, identify, quantify, neutralize or destroy an analyte. Non-limiting examples of analytes include a toxin, poison, allergen, virus, bacterium, spore or other biological or chemical agent.

"Aptamer" means a nucleic acid that binds to another molecule ("target," as defined below). This binding interaction does not encompass standard nucleic acid/nucleic acid hydrogen bond formation exemplified by Watson-Crick basepair formation (e.g., A binds to U or T and G binds to C), but encompasses all other types of non-covalent (or in some cases covalent) binding. Non-limiting examples of non-covalent binding include hydrogen bond formation, electrostatic interaction, Van der Waals interaction and hydrophobic interaction. An aptamer may bind to another molecule by any or all of these types of interaction, or in some cases by covalent interaction. Covalent binding of an aptamer to another molecule may occur where the aptamer or target molecule contains a chemically reactive or photoreactive moiety. The term "aptamer" refers to a nucleic acid that is capable of forming a complex with an intended target substance. "Target-specific" means that the aptamer binds to a target analyte with a much higher degree of affinity than it binds to contaminating materials.

"Analyte," "target" and "target analyte" mean any compound or aggregate of interest. Non-limiting examples of analytes include a protein, peptide, carbohydrate, polysaccharide, glycoprotein, lipid, hormone, receptor, antigen, allergen, antibody, substrate, metabolite, cofactor, inhibitor, drug, pharmaceutical, nutrient, toxin, cholera toxin, Shiga-like toxin, poison, explosive, pesticide, chemical warfare agent, biohazardous agent, prion, radioisotope, vitamin, heterocyclic aromatic compound, carcinogen, mutagen, narcotic, amphetamine, barbiturate, hallucinogen, waste product, contaminant or other molecule. Molecules of any size can serve as targets. "Analytes" are not limited to single molecules, but may also comprise complex aggregates of molecules, such as a virus, bacterium, spore, mold, yeast, algae, amoebae, dinoflagellate, unicellular organism, pathogen, cell or infectious agent. In certain embodiments, cells exhibiting a particular characteristic or disease state, such as a cancer cell, may be target analytes. Virtually any chemical or biological effector would be a suitable target. In particularly preferred embodiments, the analyte is anthrax.

Non-limiting examples of infectious agents within the meaning of "analyte" include the following.

| | |
|---|---|
| Actinobacillus spp. | Bacteroides spp. |
| Actinomyces spp. | Balantidium coli |
| Adenovirus (types 1, 2, 3, 4, 5 et 7) | Bartonella bacilliformis |
| Adenovirus (types 40 and 41) | Blastomyces dermatitidis |
| Aerococcus spp. | Bluetongue virus |
| *Aeromonas hydrophila* | *Bordetella bronchiseptica* |
| *Ancylostoma duodenale* | *Bordetella pertussis* |
| *Angiostrongylus cantonensis* | *Borrelia burgdorferi* |
| *Ascaris lumbricoides* | *Branhamella catarrhalis* |
| Ascaris spp. | Brucella spp. |
| Aspergillus spp. | *B. abortus* |
| *Bacillus anthracis* | *B. canis,* |
| *Bacillus cereus* | *B. melitensis* |
| *B. suis* | Ebola virus |
| Brugia spp. | *Echinococcus granulosus* |
| *Burkholderia mallei* | *Echinococcus multilocularis* |
| *Burkholderia pseudomallei* | Echovirus |
| *Campylobacter fetus* subsp. *fetus* | *Edwardsiella tarda* |
| *Campylobacter jejuni* | *Entamoeba histolytica* |
| *C. coli* | Enterobacter spp. |
| *C. fetus* subsp. *jejuni* | Enterovirus 70 |
| *Candida albicans* | *Epidermophyton floccosum,* |
| Capnocytophaga spp. | Microsporum spp. Trichophyton spp. |
| *Chlamydia psittaci* | Epstein-Barr virus |
| *Chlamydia trachomatis* | *Escherichia coli,* |
| | *enterohemorrhagic* |
| Citrobacter spp. | *Escherichia coli,* enteroinvasive |
| *Clonorchis sinensis* | *Escherichia coli,* |
| | *enteropathogenic* |
| *Clostridium botulinum* | *Escherichia coli,* enterotoxigenic |
| *Clostridium difficile* | *Fasciola hepatica* |
| *Clostridium perfringens* | *Francisella tularensis* |
| *Clostridium tetani* | Fusobacterium spp. |
| Clostridium spp. | *Gemella haemolysans* |
| *Coccidioides immitis* | *Giardia lamblia* |
| Colorado tick fever virus | Giardia spp. |
| *Corynebacterium diphtheriae* | *Haemophilus ducreyi* |
| *Coxiella burnetii* | *Haemophilus influenzae* (group b) |
| Coxsackievirus | Hantavirus |
| Creutzfeldt-Jakob agent, Kuru agent | Hepatitis A virus |
| Crimean-Congo hemorrhagic fever virus | Hepatitis B virus |
| | Hepatitis C virus |
| *Cryptococcus neoformans* | Hepatitis D virus |
| *Cryptosporidium parvum* | Hepatitis E virus |
| Cytomegalovirus | Herpes simplex virus |
| Dengue virus (1, 2, 3, 4) | *Herpesvirus simiae* |
| Diphtheroids | *Histoplasma capsulatum* |
| Eastern (Western) equine encephalitis virus | Human coronavirus |
| | Human immunodeficiency virus |
| Human papillomavirus | Peptococcus spp. |
| Human rotavirus | Peptostreptococcus spp. |
| Human T-lymphotrophic virus | *Plesiomonas shigelloides* |
| Influenza virus | *Powassan encephalitis* virus |
| Junin virus/Machupo virus | Proteus spp. |
| Klebsiella spp. | Pseudomonas spp. |
| Kyasanur Forest disease virus | Rabies virus |
| Lactobacillus spp. | Respiratory syncytial virus |
| *Legionella pneumophila* | Rhinovirus |
| Leishmania spp. | *Rickettsia akari* |
| *Leptospira interrogans* | *Rickettsia prowazekii, R. canada* |
| *Listeria monocytogenes* | *Rickettsia rickettsii* |
| *Lymphocytic choriomeningitis* virus | Ross river virus/O'Nyong-Nyong virus |
| Marburg virus | Rubella virus |
| Measles virus | *Salmonella choleraesuis* |
| Micrococcus spp. | *Salmonella paratyphi* |
| Moraxella spp. | *Salmonella typhi* |
| Mycobacterium spp. | Salmonella spp. |
| Mycobacterium tuberculosis, *M. bovis* | Schistosoma spp. |
| *Mycoplasma hominis, M. orale, M. salivarium, M. fermentans* | Scrapie agent |
| | Serratia spp. |
| *Mycoplasma pneumoniae* | Shigella spp. |
| *Naegleria fowleri* | Sindbis virus |
| *Necator americanus* | *Sporothrix schenckii* |
| *Neisseria gonorrhoeae* | St. Louis encephalitis virus |
| *Neisseria meningitidis* | Murray Valley encephalitis virus |
| Neisseria spp. | *Staphylococcus aureus* |

-continued

| | |
|---|---|
| Nocardia spp. | *Streptobacillus moniliformis* |
| Norwalk virus | *Streptococcus agalactiae* |
| Omsk hemorrhagic fever virus | *Streptococcus faecalis* |
| *Onchocerca volvulus* | *Streptococcus pneumoniae* |
| Opisthorchis spp. | *Streptococcus pyogenes* |
| Parvovirus B19 | *Streptococcus salivarius* |
| Pasteurella spp. | *Taenia saginata* |
| | *Taenia solium* |
| | Varicella-zoster virus |
| *Toxocara canis, T. cati* | Venezuelan equine encephalitis |
| *Toxoplasma gondii* | Vesicular stomatitis virus |
| *Treponema pallidum* | *Vibrio cholerae, serovar* 01 |
| Trichinella spp. | *Vibrio parahaemolyticus* |
| *Trichomonas vaginalis* | *Wuchereria bancrofti* |
| *Trichuris trichiura* | Yellow fever virus |
| *Trypanosoma brucei* | *Yersinia enterocolitica* |
| *Ureaplasma urealyticum* | *Yersinia pseudotuberculosis* |
| Vaccinia virus | *Yersinia pestis* |

"Binding" refers to an interaction or binding between a target and a nucleic acid ligand or aptamer, resulting in a sufficiently stable complex so as to permit separation of nucleic acid ligand:target complexes from uncomplexed nucleic acid ligands under given binding or reaction conditions. Binding is mediated through hydrogen bonding, electrostatic interaction, hydrophobic interaction, Van der Walls forces or other molecular forces. In certain embodiments, binding may be covalent, for example where the nucleic acid ligand or analyte contains a photoreactive or chemically reactive moiety to promote covalent attachment of ligand and analyte. Covalent binding may be desirable, for example, where an analyte or ligand is labeled to facilitate purification of the analyte:ligand pair.

"Organic semiconductor" means a conjugated (alternating double and single bonded) organic compound in which regions of electrons and the absence of electrons (holes or positive charges) can move with varying degrees of difficulty through the aligned conjugated system (varying from insulator to conductor). An organic semiconductor may be thought of as the organic equivalent of a metal, in terms of electrical properties. Organic semiconductors are distinguished from metals in their spectroscopic properties. Organic semiconductors of use in the practice of the instant invention may be fluorescent, luminescent, chemiluminescent, sonochemiluminescent, thermochemiluminescent or electrochemiluminescent or may be otherwise characterized by their absorption, reflection or emission of electromagnetic radiation, including infrared, ultraviolet or visible light. In certain embodiments, the organic semiconductor is DALM, although alternative forms of organic semiconductor are contemplated within the scope of the invention.

"Recognition complex" refers to a nucleic acid ligand that is operably coupled to an organic semiconductor. "Operably coupled" means that the nucleic acid ligand and the organic semiconductor are in close physical proximity to each other, such that binding of an analyte to the nucleic acid ligand results in a change in the properties of the organic semiconductor that is detectable as a signal. In preferred embodiments, the signal is an electrochemical signal, such as a photochemical signal, a fluorescent signal, a luminescent signal, a change of color or a change in electrical conductivity. In one preferred embodiment, the signal is a change in the fluorescence emission profile of the organic semiconductor/nucleic acid ligand couplet. Operable coupling may be accomplished by a variety of interactions, including but not limited non-covalent or covalent binding of the organic semiconductor to the nucleic acid ligand. In another embodiment, the nucleic acid ligand may be at least partially embedded in the organic semiconductor. Virtually any type of interaction between the organic semiconductor and the nucleic acid ligand is contemplated within the scope of the present invention, so long as the binding of an analyte to the nucleic acid ligand results in a change in the properties of the organic semiconductor. In one preferred embodiment, the nucleic acid ligand is electrostatically linked to the organic semiconductor by a magnesium ion bridge. In an alternate embodiment, the nucleic acid ligand is covalently linked to the semiconductor by chemical cross-linking. A number of suitable chemical cross-linking reagents are well known in the art, such as EDC (1-ethyl-3-(2-dimethylaminopropyl)carbodiimide).

A "recognition complex system" comprises an array of recognition complexes. In preferred embodiments, the array of recognition complexes is operably coupled to a detection unit, such that changes in the electrochemical properties of the organic semiconductor that result from binding of analyte to nucleic acid ligand may be detected by the detection unit. It is contemplated within the scope of the present invention that detection may be an active process or a passive process. For example, in embodiments where the array of recognition complexes is incorporated into a card or badge, the binding of analyte may be detected by a change in color of the card or badge. In other embodiments, detection occurs by an active process, such as scanning the fluorescence emission profile of an array of recognition complexes.

"Electrochemical" is used in a broad sense to mean any process involving a transfer of electrons, including reduction-oxidation chemistry of any sort. "Electrochemical" specifically includes photo-induced oxidation and reduction.

"Photochemical" means any light related or light induced chemistry. A "photochemical signal" specifically includes, but is not limited to, a fluorescent signal, a luminescent signal, a change of color, a change in electrical conductivity, photo-oxidation and photo-reduction.

"Magnetic bead," "magnetic particle" and "magnetically responsive particle" are used herein to mean any particle dispersible or suspendable in aqueous media, without significant gravitational settling and separable from suspension by application of a magnetic field. The particles comprise a magnetic metal oxide core, often surrounded by an adsorptively or covalently bound sheath or coat bearing functional groups to which various molecules, such as DALM or DNA, may be covalently coupled or adsorbed.

In certain embodiments, non-magnetic beads, such as functionalized or non-functionalized glass, or functionalized or non-functionalized polystyrene, may be used as surfaces for the attachment of recognition complexes and the separation of recognition complexes bound to analyte from complexes that do not bind analyte.

Recognition Complex System

An embodiment of the instant invention relates to compositions and apparatus capable of undergoing a process that selectively amplifies nucleic acid ligands that bind to a target analyte. This recognition complex system comprises an array of recognition complexes, each recognition complex comprising a nucleic acid ligand. In various embodiments, the nucleic acid ligand may be attached to an organic semiconductor, such as DALM. In certain embodiments, the recognition complexes are arranged in a two-dimensional array, that may be attached to a glass or other flat surface. In other embodiments, the recognition complexes comprise nucleic acid ligands attached to magnetic bead or to non-magnetic beads, such as glass, polystyrene, or polyacrylamide beads, in a three-dimensional array. In a preferred embodiment, the beads are suspended in a liquid medium.

The array of recognition complexes is exposed to analyte. Binding of analyte to individual recognition complexes is detected by, for example, changes in the electrical or photochemical properties of the recognition complex upon binding to the analyte. Where the recognition complexes comprise an organic semiconductor, such as DALM, the changes in electrical or photochemical properties may be detected by a variety of techniques, described in detail below.

In certain embodiments, an iterative process may be used to increase the specificity of the array of recognition complexes for the analyte. In each round of iteration, the array is exposed to the analyte. Recognition complexes that bind to the analyte are separated from recognition complexes that do not bind to the analyte. Methods for separating bound from unbound recognition complexes are also described in detail below. The nucleic acid ligands from recognition complexes that bind to the analyte are amplified, for example by PCR, and used to make a new array of recognition complexes. The new array will contain a higher proportion of recognition complexes that bind to the analyte, producing a stronger and more specific electrical or photochemical signal. As discussed below, certain aspects of this process resemble SELEX technology (Tuerk and Gold, 1990; Klug and Famulok, 1994; Tuerk, 1993, 1997, U.S. Pat. Nos. 5,270,163; 5,475,096; 5,567,588; 5,580,737; 5,595,877; 5,641,629; 5,650,275; 5,683,867; 5,696,249; 5,707,796; 5,763,177; 5,817,785; 5,874,218; 5,958,691; 6,001,577; 6,030,776; each incorporated herein by reference). With each round of iteration, a set of nucleic acid ligands will be produced that bind to the analyte with greater affinity. This iterative process may also be used to produce nucleic acid ligands that bind to the analyte with high affinity. Such high affinity nucleic acid ligands will be useful in numerous applications, described below. One such application involves production of a neutralizing agent that can inactivate or destroy the target analyte.

Embodiments Involving a Chip Type of Array

FIG. 1 illustrates a recognition complex system in accordance with an exemplary embodiment of the present invention. This embodiment of the recognition complex system includes a sample collection unit 105, an analyte isolation unit 110, an organic semiconductor chip based array of recognition complexes 115, a detection unit 120 and a data storage and processing unit 125. In general, the sample collection unit 105 is employed to actively collect or passively receive samples containing the unknown analyte to be identified. The analyte isolation unit 110 is employed to filter the sample and isolate the unknown analyte from other substances or compounds that might be present in the sample. The sample collection unit 105 and the analyte isolation unit 110 may be implemented in accordance with any number of known techniques and/or components known in the art.

The array of recognition complexes 115 comprises one or more individual recognition complexes 130. It will be understood that the array of recognition complexes 115 is shown as comprising 15 recognition complexes for illustrative purposes only. In actuality, the array 115 may contain significantly more than 15 recognition complexes. Within the scope of the invention, the array may comprise approximately 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 125, 130, 140, 150, 160, 170, 175, 180, 185, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 6000, 7000, 8000, 9000, 10000, 15000, 20000, 30000, 40000, 50000, 75000, 10000, 20000, 30000, 40000, 50000, 100000, 200000, 500000, $10^6$, $10^7$, $10^8$, $10^9$, $10^{10}$, $10^{11}$, $10^{12}$, $10^{14}$, $10^{16}$, $10^{18}$, $10^{20}$, $10^{22}$, up $10^{24}$ recognition complexes or any number in between. In certain embodiments, the nucleic acid ligand component of each recognition complex differs in sequence from the nucleic acid ligand component of the other recognition complexes in the array. In other embodiments, some or all of the nucleic acid ligands may be similar or identical in sequence.

Each of the recognition complexes 130 associated with the array 115 comprises a nucleic acid ligand/organic semiconductor couplet. In a preferred embodiment, the couplet is sandwiched between a pair of electrodes, one of which is preferably transparent. The recognition complexes may be sandwiched between two electrodes with (for alternating current or forward and reverse DC bias) or without (for DC only) intervening insulating layers. This embodiment provides a recognition complex system formed from a miniaturized array of light-emitting diodes. One of the electrodes is transparent to allow for the passage of light. The other electrode is made of a conductive substance such as copper, aluminum, or gold.

In certain embodiments, the organic semiconductor used in diazoluminomelanin (DALM). DALM is a polymer that exhibits slow fluorescent, chemiluminescent, sonochemiluminescent, thermochemiluminescent and electrochemiluminescent properties (Bruno and Yu, 1996). However, other organic semiconductors may serve as acceptable substitutes, in particular, polyphenylenes. A non-limiting example of a polyphenylene that might be used within the scope of the instant invention is poly(para-phenylenevinylene) (Kugler et al., 1999).

As shown in FIG. 1, the recognition complex system comprises an array 115 of recognition complexes, such as recognition complex 130. Each of these recognition complexes comprises a nucleic acid ligand/organic semiconductor couplet. Separating each of the recognition complexes is binding material. The nucleic acid ligand sequences present at each of the recognition complexes may be random sequences. In an exemplary embodiment, the nucleic acid ligand sequences may be distributed across the array as a function of charge and size, or alternatively as a function of charge and pI (isoelectric point).

After collecting and isolating the unknown analyte, the analyte is applied to each recognition complex associated with the array 115. In those embodiments where the nucleic acid ligand sequences are not identical, some of the nucleic acid ligands will exhibit a high affinity for the analyte, some nucleic acid ligands will exhibit less affinity for the analyte and some nucleic acid ligands will exhibit no affinity for the analyte. The electrochemical properties of the nucleic acid ligand/organic semiconductor couplet will change depending on the degree to which the nucleic acid ligands bind to the analyte. The electrotochemical properties associated with some recognition complexes will change significantly, while the electrochemical properties associated with other recognition complexes may change very little, if at all, upon exposure to a given analyte.

In accordance with one exemplary embodiment, one of the electrodes associated with each recognition complex is transparent. The transparency of this electrode permits excitation energy, such as light, to be transmitted through each recognition complex. In a preferred embodiment, ultraviolet light is employed. The passage of ultra-violet or other frequency irradiation through each of the recognition complexes 130 may permit detection unit 120 to more easily detect and quantify any electrochemical changes that take place at each recognition complex 130 as a result of binding to the analyte. The electrochemical changes may involve changes in the color of the nucleic acid ligand/organic semiconductor couplet and/or changes in the color intensity. In preferred embodiments, the detection unit 120 comprises a charge coupled device (CCD), such as a CCD camera, digital camera, photomultiplier tube or any other functionally equivalent detector.

The electrochemical signature of the analyte may consist of a two-dimensional distribution of fluorescence resulting from long-wavelength ultraviolet light excitation. Response of the array 115 at a specific spatial location 130 may be similar for two or more different analytes, but by combining the fluorescence response of many independent measurement locations, specificity can be high. A typical consumer-type CCD-based color video camera has 768×494 discrete detectors. A miniaturized cell utilizing such a camera with an array could have about 380,000 parallel channels (single detectors). Practical considerations would group detectors for lower but less spatially noisy resolution with fewer channels. Hundreds to thousands of channels could easily be achieved. Optimization of the number of channels would minimize channels and thus computational load, while maximizing specificity and classification accuracy.

Analysis of the photochemical signature, by data processing unit 125, may involve a comparison of multiple channels of fluorescence spectral signatures. Comparison of signatures by data processing unit 125 may be implemented using artificial neural networks (such as the Qnet v2000 neural net software package from Vesta Services, Inc., 1001 Green Bay Rd., Winnetka, Ill. 60093). This would provide a fast comparison of unknown analytes to a database of previously recorded signatures of known analytes.

Any binding between the analyte and the nucleic acid ligand associated with a given recognition complex may alter the electrical properties of the corresponding nucleic acid ligand/organic semiconductor couplet. In another exemplary embodiment, a voltage is applied across each recognition complex of the array 115 after the analyte has been introduced. The amount of current that is able to flow across each recognition complex is a function of the conductivity of the nucleic acid ligand/organic semiconductor couplet. Changes in conductivity of each couplet upon binding of analyte may be stored and analyzed to identify the analyte.

In certain embodiments, voltage may be applied across each of the recognition complexes in addition to exciting each recognition complex with ultraviolet or other frequency irradiation. In such embodiments, changes in both the electrical properties and the photochemical properties of each recognition complex may be detected and analyzed. These combined data may more readily establish a unique signature for identifying the analyte. In these embodiments, the detection unit 120 would have to include the ability to detect both changes in current and photochemical changes at each of the recognition complexes. Application of a current flowing through the recognition complexes may result in the enhancement of any photochemical changes that take place as a result of analyte/nucleic acid ligand binding, thereby making it easier for the detection unit 120 to detect and quantify those photochemical changes.

In accordance with one aspect of the present invention, unknown chemical and biological analytes may be detected and identified in a single, automated binding step, as the reaction between the analyte and the nucleic acid ligand sequences distributed across the array 115 produces a relatively unique change in the electrochemical properties of the array as a whole. However, where two or more analytes share similar chemical structures, they might cause the array 115 to produce a relatively similar electrochemical response.

Thus, in accordance with another aspect of the present invention, a more unique electrochemical response from the array 115 can be achieved to more clearly distinguish between structurally similar analytes. To accomplish this, the nucleic acid ligands associated with those recognition complexes that bind to the analyte, as indicated by changes in electrochemical properties, may extracted from the array.

In certain embodiments, individual recognition complexes 130 may be detached from the array 115 by hydrolysis, cleavage, heating or other methods of dissociation applied to the array at the location of each such recognition complex. The nucleic acid ligand sequences exhibiting affinity for analyte may be separated from the analyte by washing the nucleic acid ligand bound to analyte with deionized water, salt solutions, detergents, chaotrophic agents, solvents or other solutions that serve to separate the analyte from ligand. The nucleic acid ligand sequences that exhibit no affinity for the analyte can be discarded. The extracted nucleic acid ligand sequences may be amplified and applied to a clean chip to produce a new array 115. Since the new array 115 comprises only those nucleic acid ligand sequences that were identified as binding to the analyte, it should exhibit a greater degree of specificity and a higher binding affinity for the analyte.

As the process of amplification inherently produces some variation in the amplified nucleic acid ligand sequences, due to the normal error rate of DNA or RNA polymerase, the amplified nucleic acid ligands may exhibit some sequences that were not present on the initial array, although they will generally be identical or almost identical in sequence to the original nucleic acid ligands. These sequence variants may also exhibit variability in their binding affinity for the analyte, with some sequence variants exhibiting an increased affinity for analyte. The iterative process may be used to select for nucleic acid ligand sequences that bind to analyte with higher affinity with each round of iteration. The skilled artisan will realize that use of polymerases with a greater inherent error rate, or manipulation of amplification conditions to increase the error rate, may be desirable in certain embodiments of the present invention.

Once a new array chip 115 is produced, analyte may be introduced to each of the array recognition complexes 130, and the electrochemical changes across the array may be detected and analyzed, producing an even more unique signature that can be used for analyte identification and to distinguish the analyte from chemically or structurally similar species.

The production of chips for attachment of nucleic acid ligands is well known in the art. The chip may comprise a Langmuir-Bodgett film, functionalized glass, germanium, silicon, PTFE, polystyrene, gallium arsenide, gold, silver, membrane, nylon, PVP, or any other material known in the art that is capable of haying functional groups such as amino, carboxyl, Diels-Alder reactants, thiol or hydroxyl incorporated on its surface. In certain embodiments, these groups may be covalently attached to cross-linking agents so that binding interactions between analyte and recognition complex occur without steric hindrance from the chip surface. Typical cross-linking groups include ethylene glycol oligomer, diamines and amino acids. Any suitable technique useful for immobilizing a recognition complex on a chip is contemplated by this invention, including sialinization. In certain embodiments, DALM is attached to the chip surface and nucleic acid ligands are then attached, covalently or non-covalently, to the DALM.

The array-based chip design 115 may be distinguished from conventional biochips (e.g., U.S. Pat. Nos. 5,861,242 and 5,578,832) by a number of characteristics, including the use of an organic semiconductor, such as DALM. Additionally, conventional biochips typically are constructed by attaching or synthesizing nucleic acid ligands having affinities for known analytes on specific identified locations on the chip. The presence of a target analyte in a sample is detected by binding to the specific chip locus containing a nucleic acid ligand with known affinity for that analyte. In contrast, in certain embodiments of the present invention the affinities of the nucleic acid ligand/organic semiconductor couplets for various analytes are unknown at the time they are initially attached to the chip. Target analytes are identified by their pattern of binding to the entire chip, not by their binding to a specific locus on the chip. This system provides greater efficiency and flexibility, in that it is not necessary to prepare nucleic acid ligands of known specificity before construction of the chip. Further, previously unknown analytes may be characterized by their pattern of interaction with the chip, without having to clone and sequence their RNA or DNA or prepare high-affinity aptamers in advance of chip production.

This is not meant to exclude the possibility of selecting for the presence of one or more nucleic acid ligands with higher affinity for the target. Such higher affinity nucleic acid ligands may be used to generate a new array 115 with increased affinity or specificity for the target. That capability further distinguishes the present invention from conventional biochips, which do not utilize iterative amplification of selected nucleic acid ligands to generate new chips with higher specificity or affinity for a target analyte.

Embodiments Involving Magnetic Beads

In an alternative embodiment, the nucleic acid ligand sequences may be attached to magnetic beads instead of to a glass or other flat surface. In this case, each recognition complex would comprise a magnetic bead attached to one or more nucleic acid ligands. In a preferred embodiment, each nucleic acid ligand molecule attached to the same magnetic bead will have the same sequence. In other embodiments, the nucleic acid ligand molecules attached to a single bead may have different sequences. In certain preferred embodiments, the nucleic acid ligands will also be attached to an organic semiconductor, such as DALM. Attachment of nucleic acid ligands to DALM would facilitate the detection and quantitation of analyte binding to the nucleic acid ligands, as described above.

The skilled artisan will realize that use of magnetic bead technology would facilitate certain applications of the invention, such as the iterative process for producing nucleic acid ligands of higher specificity and greater binding affinity for the analyte. With magnetic bead technology, the individual recognition complexes are more easily manipulated and separated according to their characteristics. For example, recognition complexes that bind to the analyte may be separated from recognition complexes that do not bind to the analyte by using a magnetic flow cell or filter block, as disclosed in U.S. Pat. No. 5,972,721, incorporated herein by reference in its entirety.

Figure 2:
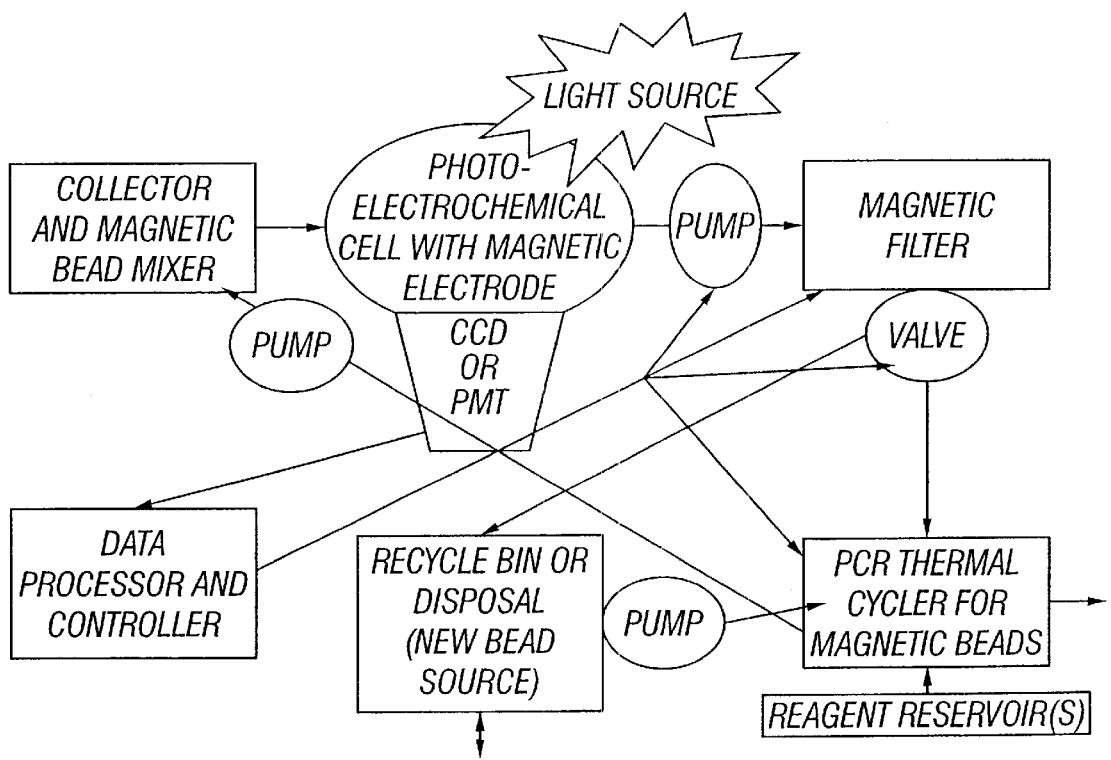
FIG. 2 illustrates another exemplary embodiment of a recognition complex system, using recognition complexes attached to magnetic beads. The flow chart illustrates the operational relationships between the components of a preferred embodiment of a recognition complex system.

A diagram for use of magnetic beads in a recognition complex system is shown in FIG. 2. Nucleic acid ligands of random or non-random sequence may be synthesized or amplified and attached to magnetic beads. The individual recognition complexes, each corresponding to a magnetic bead attached to one or more nucleic acid ligands, together comprise an array, similar to that described above for FIG. 1. The array is added to the magnetic bead mixer (FIG. 2) and analyte is added and allowed to bind to the nucleic acid ligands. The mixture is then transferred to a photoelectrochemical cell with a magnetic electrode, where the mixture may be exposed to ultraviolet or other irradiation. A CCD, photomultiplier tube, digital camera or other detection device may be used to obtain absorption or emission spectra. As described above, binding of analyte will result in characteristic changes in the photochemical properties of individual recognition complexes. These changes in photochemical properties will be detected and analyzed to produce an analyte signature, as described above. Although the suspension of recognition complexes in the bead mixer is random, the use of a magnetic electrode in the photoelectrochemical cell will provide a spatial distribution of recognition complexes, analogous to the two-dimensional array 115 described above. Beads will deposit and separate on the surface of the magnetic electrode according to their accumulated mass (from binding analyte). This spatial distribution, along with the detected photochemical changes, may be analyzed to produce a unique signature that can be used to identify the analyte.

After detection, the recognition complexes may be transferred to a magnetic filter (FIG. 2), where the recognition complexes that bind to the analyte may be separated from those that do not bind analyte. The recognition complexes that do not bind analyte are transferred to the recycle bin (FIG. 2), where the nucleic acid ligands may be detached from the magnetic beads. The magnetic beads may be disposed of or recycled for attachment to new nucleic acid ligands. Those recognition complexes that bind to the analyte may be transferred to a PCR cycler (FIG. 2), where the nucleic acid ligand sequences may be amplified. The new nucleic acid ligand sequences are attached to magnetic beads and transferred to the magnetic bead mixer (FIG. 2) for another iteration of the process. This iterative process may be used to produce nucleic acid ligands that bind with high affinity to the analyte, or may be used to produce an array with greater specificity for the target analyte. Certain components that may be incorporated into a recognition complex system as shown in FIG. 2 include pumps and valves to facilitate fluid transfer between different components of the recognition complex system. It is anticipated that virtually any pump or valve capable of producing a controlled fluid transfer between one component and another component of the recognition complex system illustrated in FIG. 2 could be used.

Figure 3:
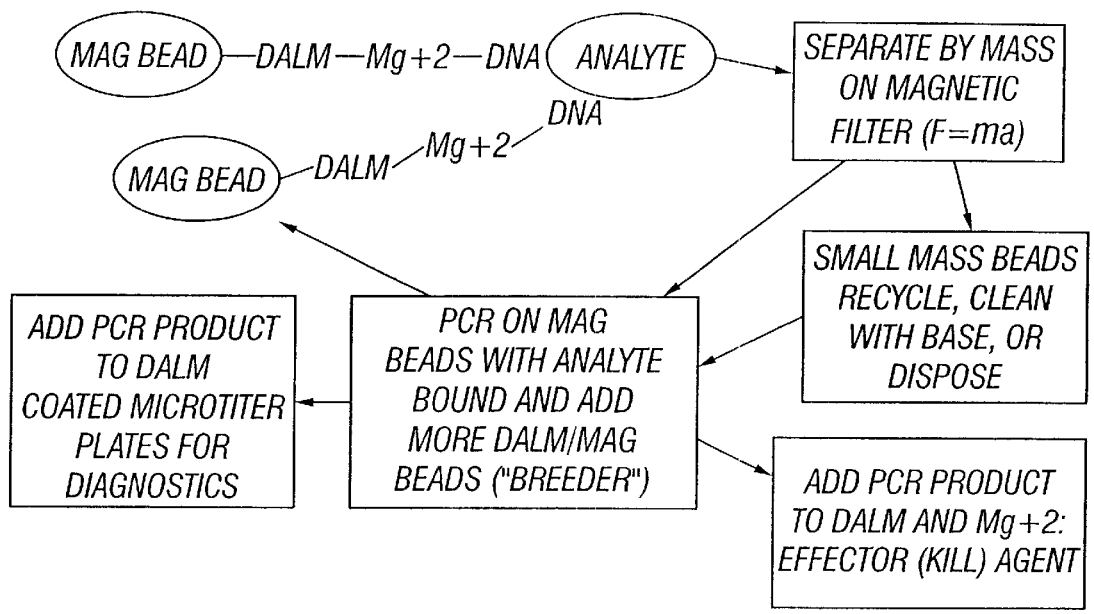
FIG. 3 illustrates a process for separation of recognition complexes, comprising magnetic beads, that bind analyte from those that do not, as well as an iterative process for producing nucleic acid ligands that bind to an analyte with high affinity.

Processes for the coupling of molecules to magnetic beads or a magnetite substrate are well known in the art, i.e. U.S. Pat. Nos. 4,695,393, 3,970,518, 4,230,685, and 4,677,055 herein expressly incorporated by reference. Alternatively, an organic semiconductor such as DALM may be attached directly to the magnetic bead. Nucleic acid ligands, such as DNA, may be attached to DALM by electrostatic interaction with magnesium ion (FIG. 3). This would facilitate detachment of DNA from the DALM/magnetic bead, since DNA would be released by addition of a chelating agent such as EDTA (ethylene diamine tetraacetic acid). Alternatively, the nucleic acid ligand may be covalently attached, for example by chemical cross-linking to DALM through the use of any appropriate cross-linking agent known in the art, such as EDC.

As shown in FIG. 3, the analyte may bind to one or more recognition complexes. Those recognition complexes bound to the analyte may be separated from unbound recognition complexes by mass segregation, using a magnetic filter (see FIG. 2). The nucleic acid ligands (indicated in FIG. 3 as DNA) with affinity for analyte may be amplified by PCR or other methods described below. The amplified nucleic acid ligands may be attached to DALM and/or magnetic beads for another iteration of analyte binding and detection, or may be collected and used for other purposes, such as analyte neutralization or preparation of high-affinity diagnostic devices for detecting analyte in the field (FIG. 3).

It is envisioned that particles employed in the instant invention may come in a variety of sizes. While large magnetic particles (mean diameter in solution greater than 10 $\mu$m) can respond to weak magnetic fields and magnetic field gradients, they tend to settle rapidly, limiting their usefulness for reactions requiring homogeneous conditions. Large particles also have a more limited surface area per weight than smaller particles, so that less material can be coupled to them. In preferred embodiments, the magnetic beads are less than 10 $\mu$m in diameter.

Various silane couplings applicable to magnetic beads are discussed in U.S. Pat. No. 3,652,761, incorporated herein by reference. Procedures for silanization known in the art generally differ from each other in the media chosen for the polymerization of silane and its deposition on reactive surfaces. Organic solvents such as toluene (Weetall, (1976)), methanol, (U.S. Pat. No. 3,933,997) and chloroform (U.S. Pat. No. 3,652,761) have been used. Silane deposition from aqueous alcohol and aqueous solutions with acid have also been used.

Ferromagnetic materials in general become permanently magnetized in response to magnetic fields. Materials termed "superparamagnetic" experience a force in a magnetic field gradient, but do not become permanently magnetized. Crystals of magnetic iron oxides may be either ferromagnetic or superparamagnetic, depending on the size of the crystals. Superparamagnetic oxides of iron generally result when the crystal is less than about 300 angstroms (Å) in diameter; larger crystals generally have a ferromagnetic character.

Dispersible magnetic iron oxide particles reportedly having 300 Å diameters and surface amine groups were prepared by base precipitation of ferrous chloride and ferric chloride ($Fe^{2+}/Fe^{3+}=1$) in the presence of polyethylene imine, according to U.S. Pat. No. 4,267,234. These particles were exposed to a magnetic field three times during preparation and were described as redispersible. The magnetic particles were mixed with a glutaraldehyde suspension polymerization system to form magnetic polyglutaraldehyde microspheres with reported diameters of 0.1 $\mu$m. Polyglutaraldehyde microspheres have conjugated aldehyde groups on the surface which can form bonds to amino containing molecules such as proteins.

While a variety of particle sizes are envisioned to be applicable in the disclosed method, in a preferred embodiment, particles are between about 0.1 and about 1.5 $\mu$m diameter. Particles with mean diameters in this range can be produced with a surface area as high as about 100 to 150 $m^2$/gm, which provides a high capacity for bioaffinity adsorbent coupling. Magnetic particles of this size range overcome the rapid settling problems of larger particles, but obviate the need for large magnets to generate the magnetic fields and magnetic field gradients required to separate smaller particles. Magnets used to effect separations of the magnetic particles of this invention need only generate magnetic fields between about 100 and about 1000 Oersteds. Such fields can be obtained with permanent magnets which are preferably smaller than the container which holds the dispersion of magnetic particles and thus, may be suitable for benchtop use. Although ferromagnetic particles may be useful in certain applications of the invention, particles with superparamagnetic behavior are usually preferred since superparamagnetic particles do not exhibit the magnetic aggregation associated with ferromagnetic particles and permit redispersion and reuse.

The method for preparing the magnetic particles may comprise precipitating metal salts in base to form fine magnetic metal oxide crystals, redispersing and washing the crystals in water and in an electrolyte. Magnetic separations may be used to collect the crystals between washes if the crystals are superparamagnetic. The crystals may then be coated with a material capable of adsorptively or covalently bonding to the metal oxide and bearing functional groups for coupling with nucleic acid ligands or DALM.

Embodiments Involving Non-Magnetic Beads, Cells or Particles and Flow Cytometry

In another embodiment, the recognition complexes or analyte of interest may be non-covalently or covalently attached to non-magnetic beads, such as glass, polyacrylamide, polystyrene or latex. Receptor complexes may be attached to such beads by the same techniques discussed above for magnetic beads. After exposure of analyte to receptor complexes, those complexes bound to analyte may be separated from unbound complexes by flow cytometry. Non-limiting examples of flow cytometry methods are disclosed in Betz et al. (1984), Wilson et al. (1988), Scillian et al. (1989), Frengen et al. (1994), Griffith et al. (1996), Stuart et al. (1998) and U.S. Pat. Nos. 5,853,984 and 5,948,627, each incorporated herein by reference in its entirety. U.S. Pat. Nos. 4,727,020, 4,704,891 and 4,599,307, incorporated herein by reference, describe the arrangement of the components comprising a flow cytometer and the general principles of its use.

In the flow cytometer, beads, cells or other particles are passed substantially one at a time through a detector, where each particle is exposed to an energy source. The energy source generally provides excitatory light of a single wavelength. The detector comprises a light collection unit, such as photomultiplier tubes or a charge coupled device, which may be attached to a data analyzer such as a computer. The beads, cells or particles can be characterized by their response to excitatory light, for example by detecting and/or quantifying the amount of fluorescent light emitted in response to the excitatory light. Changes in size due to binding of analyte to ligand can also be incorporated into sorting strategies. Beads or cells exhibiting a particular characteristic can be sorted using an attached cell sorter, such as the FACS Vantage™ cell sorter sold by Becton Dickinson Immunocytometry Systems (San Jose, Calif.).

This system is well suited to use with an organic semiconductor, such as DALM, that has well defined fluorescent and luminescent properties. Using a flow cytometer, it is possible to separate beads, cells or particles that are associated with recognition complexes bound to analytes, from unbound complexes, by detecting the presence of and characterizing the electrochemical properties of the organic semiconductor. Because those properties change upon binding of recognition complex to analyte, it is possible to separate bead-attached recognition complexes that bind to analyte from complexes that do not bind analyte. This process is even simpler when the analyte is incorporated into a cell or cell fragment, or attached to a bead. In this case, only analytes bound to recognition complexes should show a fluorescent or other spectroscopic signature associated with the organic semiconductor. In an alternative embodiment, the analyte or ligand may be labeled with a different fluorescent or other spectroscopic tag moiety. Many examples of fluorescent or other tag moieties are known in the art.

Flow cytometry may be used to purify or partially purify analytes that bind to a particular nucleic acid ligand, or to purify or partially purify ligands that bind to a particular analyte. Other manipulations may include sorting for differences in fluorescence and/or size that represent differences in binding affinity or avidity of analyte for ligand or the number of ligands bound to each analyte or of analyte bound to each ligand.

Nucleic Acids

Nucleic acid ligands within the scope of the present invention may be made by any technique known to one of ordinary skill in the art. Non-limiting examples of nucleic acid ligands include synthetic oligonucleotides made by in vitro chemical synthesis using phosphotriester, phosphite or phosphoramidite chemistry and solid phase techniques (EP 266,032, incorporated herein by reference) or via deoxynucleoside H-phosphonate intermediates (Froehler et al., 1986, and U.S. Pat. No. 5,705,629, each incorporated herein by reference). Examples of enzymatically produced nucleic acid ligands include those produced by amplification reactions such as PCR™ (e.g., U.S. Pat. Nos. 4,683,202 and 4,683,195, each incorporated herein by reference), or the synthesis of oligonucleotides described in U.S. Pat. No. 5,645,897, incorporated herein by reference. Examples of a biologically produced nucleic acid ligand include recombinant nucleic acid production in living cells, such as recombinant DNA vector production in bacteria (e.g., Sambrook et al. 1989).

Nucleobase, nucleoside and nucleotide mimics or derivatives are well known in the art, and have been described in exemplary references such as, for example, Scheit, Nucleotide Analogs (John Wiley, New York, 1980). Purine and pyrimidine nucleobases encompass naturally occurring purines and pyrimidines and derivatives and mimics thereof. These include, but are not limited to, purines and pyrimidines substituted with one or more alkyl, carboxyalkyl, amino, hydroxyl, halogen (i.e. fluoro, chloro, bromo, or iodo), thiol, or alkylthiol groups. The alkyl substituents may comprise from about 1, 2, 3, 4, or 5, to about 6 carbon atoms.

Examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcytosine, 5-bromouracil, 5-ethyluracil, 5-iodouracil, 5-chlorouracil, 5-propyluracil, thiouracil, 2-methyladenine, methylthioadenine, N,N-dimethyladenine, azaadenines, 8-bromoadenine, 8-hydroxyadenine, 6-hydroxyaminopurine, 6-thiopurine, 4-(6-aminohexyl/cytosine), and the like. A list of exemplary purine and pyrimidine derivatives and mimics is provided in Table 1.

TABLE 1

Purine and Pyrimidine Derivatives or Mimics

| Abbr. | Modified base description |
|---|---|
| ac4c | 4-acetylcytidine |
| chm5u | 5-(carboxyhydroxylmethyl)uridine |
| Cm | 2'-O-methylcytidine |
| cmnm5s2u | 5-carboxymethylaminomethyl-2-thioridine |
| cmnm5u | 5-carboxymethylaminomethyluridine |

TABLE 1-continued

Purine and Pyrimidine Derivatives or Mimics

| Abbr. | Modified base description |
|---|---|
| D | Dihydrouridine |
| Fm | 2'-O-methylpseudouridine |
| gal q | beta,D-galactosylqueosine |
| Gm | 2'-O-methylguanosine |
| I | Inosine |
| i6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| man q | Beta,D-mannosylqueosine |
| mcm5s2u | 5-methoxycarbonylmethyl-2-thiouridine |
| mcm5u | 5-methoxycarbonylmethyluridine |
| mo5u | 5-methoxyuridine |
| ms2i6a | 2-methylthio-N6-isopentenyladenosine |
| ms2t6a | N-((9-beta-D-ribofuranosyl-2-methylthio-purine-6-yl)carbamoyl)threonine |
| mt6a | N-((9-beta-D-ribofuranosylpurine-6-yl)N-methyl-carbamoyl)threonine |
| mv | Uridine-5-oxyacetic acid methylester |
| o5u | Uridine-5-oxyacetic acid (v) |
| osyw | Wybutoxosine |
| p | Pseudouridine |
| q | Queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-beta-D-ribofuranosylpurine-6-yl)carbamoyl)threonine |
| tm | 2'-O-methyl-5-methyluridine |
| um | 2'-O-methyluridine |
| yw | Wybutosine |
| x | 3-(3-amino-3-carboxypropyl)uridine, (acp3)u |

An example of a nucleic acid ligand comprising nucleoside or nucleotide derivatives and mimics is a "polyether nucleic acid", described in U.S. Pat. No. 5,908,845, incorporated herein by reference, wherein one or more nucleobases are linked to chiral carbon atoms in a polyether backbone. Another example of a nucleic acid ligand is a "peptide nucleic acid", also known as a "PNA", "peptide-based nucleic acid mimics" or "PENAMs", described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is not a 5-carbon sugar and/or at least one backbone moiety that is not a phosphate group. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/01219). In addition, U.S. Pat. Nos. 5,766,855, 5,719,262, 5,714,331 and 5,736,336 describe PNAs comprising nucleobases and alkylamine side chains with further improvements in sequence specificity, solubility and binding affinity. These properties promote double or triple helix formation between a target and the PNA.

The skilled artisan will realize that the present invention is not limited to the examples disclosed herein, but may include nucleobases, nucleotides and nucleic acids produced by any other means known in the art.

Amplification

In certain embodiments, the nucleic acid ligands of the recognition complex system may be amplified to provide a source of high affinity nucleic acid ligands for neutralizing analytes. Amplification may also be of use in the iterative process for generating arrays with greater specificity or binding affinity for the analyte. Within the scope of the present invention, amplification may be accomplished by any means known in the art. Exemplary embodiments are described below.

Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

Amplification Methods

A number of template dependent processes are available to amplify the marker sequnces present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference.

Briefly, in PCR, two primer sequences are prepared which are complementary to regions on opposite complementary strands of, for example, a nucleic acid ligand. An excess of deoxynucleoside triphosphates are added to a reaction mixture along with a DNA polymerase, e.g., Taq polymerase. Examples of polymerases that may be used for purposes of nucleic acid amplification are provided in Table 2 below. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the nucleic acid ligand to form reaction products, excess primers will bind to the nucleic acid ligand and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. Polymerase chain reaction methodologies are well known in the art.

Another method for amplification is the ligase chain reaction ("LCR"), disclosed in European Application No. 320,308. In LCR, two complementary probe pairs are prepared, and in the presence of the nucleic acid ligand sequence, each pair will bind to opposite complementary strands of the target such that they abut. In the presence of a ligase, the two probe pairs will link to form a single unit. By temperature cycling, as in PCR, bound ligated units dissociate from the nucleic acid ligand and then serve as templates for ligation of excess probe pairs. U.S. Pat. No. 4,883,750 describes a method similar to LCR for binding probe pairs to a nucleic acid ligand sequence.

Qbeta Replicase, described in PCT Application No. PCT/US87/00880, may also be used as still another amplification method in the present invention. In this method, a replicative sequence of RNA that has a region complementary to that of a nucleic acid ligand is added to a sample in the presence of an RNA polymerase. The polymerase will copy the replicative sequence which may then be detected.

An isothermal amplification method, in which restriction endonucleases and ligases are used to achieve the amplification of nucleic acid ligand molecules that contain nucleotide 5'-[alpha-thio]-triphosphates in one strand of a restriction site may also be useful in the amplification of nucleic acid ligands in the present invention. Walker et al., (1992).

Strand Displacement Amplification (SDA) is another method of carrying out isothermal amplification of nucleic acid ligands that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still other amplification methods described in GB Application No. 2 202 328, and in PCT Application No. PCT/US89/01025, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the nucleic acid ligand sequence is released intact to be bound by excess probe. Cleavage of the labeled probe signals the presence of the nucleic acid ligand sequence.

Other nucleic acid ligand amplification procedures include transcription-based amplification systems (TAS), including nucleic acid sequence based amplification (NASBA) and 3SR. Kwoh et al.,(1989) and PCT Application WO 88/10315. In NASBA, the nucleic acid ligands may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has nucleic acid ligand specific sequences. Following polymerization, DNA/RNA hybrids are digested with RNase H while double stranded DNA molecules are heat denatured again. In either case the single stranded DNA is made fully double stranded by addition of second nucleic acid ligand specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate nucleic acid ligand specific sequences.

Davey et al, European Application No. 329,822 disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman, (1990) and Ohara et al., (1989).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., *Genomics* 4:560 (1989).

Labels

For certain embodiments, it may be desirable to incorporate a label into nucleic acid ligands, amplification products, probes or primers. A number of different labels may be used, such as fluorophores, chromophores, radioisotopes, enzymatic tags, antibodies, chemiluminescent, electroluminescent, affinity labels, etc. One of skill in the art will recognize that these and other label moieties not mentioned herein can be used in the practice of the present invention.

Examples of affinity labels include an antibody, an antibody fragment, a receptor protein, a hormone, biotin, DNP, and any polypeptide/protein molecule that binds to an affinity label.

Examples of enzymatic tags include urease, alkaline phosphatase or peroxidase. Colorimetric indicator substrates can be employed with such enzymes to provide a detection means visible to the human eye or spectrophotometrically.

The following fluorophores are contemplated to be useful in practicing the present invention. Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Imaging Agents and Radioisotopes

In certain embodiments, the claimed nucleic acid ligands of the present invention may be attached to imaging agents of use for imaging, treatment and diagnosis of various diseased organs or tissues. Many appropriate imaging agents are known in the art, as are methods for their attachment to nucleic acids. Certain attachment methods involve the use of a metal chelate complex employing, for example, an organic chelating agent such a DTPA attached to the nucleic acid.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Methods of Immobilization

In various embodiments, the nucleic acid ligands of the present invention may be attached to a solid surface ("immobilized"). In a preferred embodiment, immobilization may occur by attachment of an organic semiconductor, such as DALM, to a solid surface, such as a magnetic, glass or plastic bead, a plastic microtiter plate or a glass slide. Nucleic acid ligands may be attached to the DALM by electrostatic interaction with magnesium ion (FIG. 3). This system is advantageous in that the attachment of nucleic acid ligand to DALM may be readily reversed by addition of a magnesium chelator, such as EDTA.

Immobilization of nucleic acid ligands may alternatively be achieved by a variety of methods involving either non-covalent or covalent interactions between the immobilized nucleic acid ligand, comprising an anchorable moiety, and an anchor. In an exemplary embodiment, immobilization may be achieved by coating a solid surface with streptavidin or avidin and the subsequent attachment of a biotinylated polynucleotide (Holmstrom, 1993). Immobilization may also occur by coating a polystyrene or glass solid surface with poly-L-Lys or poly L-Lys, Phe, followed by covalent attachment of either amino- or sulfhydryl-modified polynucleotides, using bifunctional crosslinking reagents (Running, 1990; Newton, 1993).

Immobilization may take place by direct covalent attachment of short, 5'-phosphorylated primers to chemically modified polystyrene plates ("Covalink" plates, Nunc) Rasmussen, (1991). The covalent bond between the modified oligonucleotide and the solid phase surface is formed by condensation with a water-soluble carbodiimide. This method facilitates a predominantly 5'-attachment of the oligonucleotides via their 5'-phosphates.

Nikiforov et al. (U.S. Pat. No. 5,610,287 incorporated herein by reference) describes a method of non-covalently immobilizing nucleic acid ligand molecules in the presence of a salt or cationic detergent on a hydrophilic polystyrene solid support containing an —OH, —C=O or —COOH hydrophilic group or on a glass solid support. The support is contacted with a solution having a pH of about 6 to about 8 containing the nucleic acid ligand and the cationic detergent or salt. The support containing the immobilized nucleic acid ligand may be washed with an aqueous solution containing a non-ionic detergent without removing the attached molecules.

Another commercially available method for immobilization is the "Reacti-Bind™ DNA Coating Solutions" (see "Instructions—Reacti-Bind™ DNA Coating Solution" 1/1997). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BIND™" or Immobilon-AV Affinity Membrane (IAV, Millipore, Bedford, Mass.) may be used in the practice of the instant invention.

Cross-linkers

Bifunctional cross-linking reagents may be of use in various embodiments of the claimed invention, such as attaching an organic semiconductor to a nucleic acid ligand, attaching an organic semiconductor to a substrate, attaching various functional groups to a nucleic acid ligand, or attaching a nucleic acid ligand or an analyte to a bead or particle. Homobifunctional reagents that carry two identical functional groups are highly efficient in inducing cross-linking. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, guanidino, indole, or carboxyl specific groups. Of these, reagents directed to free amino groups have become especially popular because of their commercial availability, ease of synthesis and the mild reaction conditions under which they can be applied.

Exemplary methods for cross-linking molecules, such as DALM, nucleic acid ligands or analytes, are described in U.S. Pat. Nos. 5,603,872 and 5,401,511. Various ligands can be covalently bound to surfaces through the cross-linking of amine residues. Amine residues may be introduced onto a surface through the use of aminosilane, as discussed above. Coating with aminosilane provides an active functional residue, a primary amine, on the surface for cross-linking purposes. Ligands are bound covalently to discrete sites on the surfaces. The surfaces may also have sites for non-covalent association. To form covalent conjugates of ligands and surfaces, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl)carbodiimide (EDC). Through the complex chemistry of cross-linking, linkage of the amine residues of the silane-coated surface and free DALM, nucleic acid ligand or analyte may be accomplished.

Separation and Quantitation Methods

It may be desirable to separate nucleic acid ligands of different lengths for the purpose of quantitation, analysis or purification.

Gel Electrophoresis

In one embodiment, amplification products are separated by agarose, agarose-acrylamide or polyacrylamide gel electrophoresis using standard methods (Sambrook et al., 1989). Separation by electrophoresis is based upon the differential migration through a gel according to the size and ionic charge of the molecules in an electrical field. High resolution techniques normally use a gel support for the fluid phase. Examples of gels used are starch, acrylamide, agarose or mixtures of acrylamide and agarose. Separated nucleic acids may be visualized by staining, for example with ethidium bromide. The gel may be a single concentration or gradient in which pore size decreases with migration distance. In gel electrophoresis of polynucleotides, mobility depends primarily on molecular size. In pulse field electrophoresis, two fields are applied alternately at right angles to each other to minimize diffusion mediated spread of large linear polymers.

Agarose gel electrophoresis facilitates the size-based separation of DNA or RNA in a matrix composed of a highly purified form of agar. Nucleic acids tend to become oriented in an end on position in the presence of an electric field. Migration through the gel matrices occurs at a rate inversely proportional to the $\log_{10}$ of the number of base pairs (Sambrook et al., 1989).

Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, cDNA products labeled with biotin or antigen can be captured with beads bearing avidin or antibody, respectively.

Microfluidic Techniques

Microfluidic techniques include separation on a platform such as microcapillaries, designed by ACLARA BioSciences Inc., or the LabChip™ liquid integrated circuits made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414 reports an integrated micro-PCR™ apparatus for collection and amplification of nucleic acids from a specimen. U.S. Pat. No. 5,856,174 describes an apparatus that combines the various processing and analytical operations involved in nucleic acid analysis and is incorporated herein by reference.

Capillary Electrophoresis

In some embodiments, it may be desirable to provide an additional, or alternative means for analyzing nucleic acid ligands, such as microcapillary arrays. Microcapillary array electrophoresis generally involves the use of a thin capillary or channel that may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies, 1994. Microcapillary array electrophoresis generally provides a rapid method for size-based sequencing, PCR™ product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods.

Microfabrication of microfluidic devices including microcapillary electrophoretic devices has been discussed in detail in, e.g., Jacobsen et al., 1994; Effenhauser et al., 1994; Harrison et al., 1993; Effenhauser et al., 1993; Manz et al., 1992; and U.S. Pat. No. 5,904,824, incorporated herein by reference. Typically, these methods comprise photolithographic etching of micron scale channels on silica, silicon or other crystalline substrates or chips, and can be readily adapted for use in the present invention. In some embodiments, the capillary arrays may be fabricated from the same polymeric materials described for the fabrication of the body of the device, using injection molding techniques.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acid ligands in the sample.

DALM

In certain embodiments, an organic semiconductor like DALM is used to attach nucleic acid ligands to a surface and/or to promote electrochemical detection of binding of analyte to nucleic acid ligand. Production and use of diazoluminomelanin (DALM) has previously been described in U.S. Pat. Nos. 5,856,108 and 5,003,050, incorporated herein by reference. DALM is prepared by reacting 3AT (3-amino-L-tyrosine) with an alkali metal nitrite, such as sodium nitrite, and thereafter reacting the resulting diazotized product with luminol. At some point in the reaction, the alaninyl portion of the 3AT rearranges to provide the hydroxyindole portion of the final product. It is believed that such rearrangement occurs following coupling of the luminol to the diazotized 3AT.

The reaction between 3AT and the alkali metal nitrite is carried out in aqueous medium. Since diazotization reactions are, in general, exothermic, it may be desirable to carry out this reaction under isothermal conditions or at a reduced temperature, such as, for example, at ice bath temperatures. The reaction time for the diazotization can range from about 1 to 20 minutes, preferably about 5 to 10 minutes.

Because of the relative insolubility of luminol in aqueous medium, the luminol is dissolved in an aprotic solvent, such as dimethylsulfoxide (DMSO), then added, with stirring, to the aqueous solution of diazotized 3AT. This reaction is carried out, at reduced temperature, for about 20 to 200 minutes. The solvent is then removed by evaporation at low pressure, with moderate heating, e.g., about 30° to 37° C.

The reaction mixture is acidic, having a pH of about 3.5. The coupling of the luminol and the diazotized 3AT can be facilitated by adjusting the pH of the reaction mixture to about 5.0 to 6.0.

The product DALM may be precipitated from the reaction mixture by combining the reaction mixture with an excess of a material that is not a solvent for the DALM, e.g., acetone. After centrifuging the precipitate and discarding the supernatant, the solid material may be dried under vacuum.

In general, the quantities of the 3AT, alkali metal nitrite and luminol reactants are equimolar. It is, however, within the scope of the invention to vary the quantities of the reactants. The molar ratio of 3AT:luminol may be varied over the range of about 0.6:1 to 3:1.

DALM is water soluble, having an apparent pKa for solubility about pH 5.0. DALM does not require a catalyst for chemiluminescence. The duration of the reaction is in excess of 52 hours. In contrast, luminol requires a catalyst. With micro peroxidase as the catalyst, luminol has shown peak luminescence at 1 sec and half-lives of light emission of 0.5 and 4.5 sec at pH 8.6 and 12.6, respectively. The chemiluminescence yield of DALM is better at pH 7.4 than at pH 9.5, although it still provides a strong signal at strongly basic pHs. DALM also produces chemiluminescence at pH 6.5 which is about the same intensity as that produced at pH 9.5.

DALM can be used for chemiluminescent immunoassays for biological and chemical agents; in radiofrequency and ionizing radiation dosimeters; and for RNA/DNA hybridization assays for viruses and genetic detection.

Aptamers

In certain preferred embodiments, the nucleic acid ligands to be used in the practice of the invention are aptamers. Methods of constructing and determining the binding characteristics of aptamers are well known in the art. For example, such techniques are described in Lorsch and Szostak (1996) and in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other aptamers specific for the same target. Further, the term "aptamer" specifically includes "secondary aptamers" containing a consensus sequence derived from comparing two or more known aptamers that bind to a given target.

In general, a minimum of approximately 3 nucleotides, preferably at least 5 nucleotides, are necessary to effect specific binding. The only apparent limitations on the binding specificity of the target/nucleic acid ligand complexes of the invention concern sufficient sequence to be distinctive in the binding nucleic acid ligand and sufficient binding capacity of the target substance to obtain the necessary interaction. Oligonucleotides of sequences shorter than 10 bases may be feasible if the appropriate interaction can be obtained in the context of the environment in which the target is placed. Although the nucleic acid ligands described herein are single-stranded or double-stranded, it is contemplated that aptamers may sometimes assume triple-stranded or quadruple-stranded structures.

The specifically binding nucleic acid ligands need to contain the sequence that confers binding specificity, but may be extended with flanking regions and otherwise derivatized. In preferred embodiments of the invention, the analyte-binding sequencess of aptamer binding will be flanked by known, amplifiable sequences, facilitating the amplification of the nucleic acid ligands by PCR or other amplification techniques. In a further embodiment, the flanking sequence may comprise a specific sequence that preferentially recognizes or binds a moiety to enhance the immobilization of the aptamer to a substrate.

The nucleic acid ligands found to bind to the targets may be isolated, sequenced, and/or amplified or synthesized as conventional DNA or RNA molecules. Alternatively, nucleic acid ligands of interest may comprise modified oligomers. Any of the hydroxyl groups ordinarily present in nucleic acid ligands may be replaced by phosphonate groups, phosphate groups, protected by a standard protecting group, or activated to prepare additional linkages to other nucleotides, or may be conjugated to solid supports. The 5' terminal OH is conventionally free but may be phosphorylated. Hydroxyl group substituents at the 3' terminus may also be phosphorylated. The hydroxyls may be derivatized by standard protecting groups. One or more phosphodiester linkages may be replaced by alternative linking groups. These alternative linking groups include, exemplary embodiments wherein P(O)O is replaced by P(O)S, P(O)NR$_2$, P(O)R, P(O)OR', CO, or CNR$_2$, wherein R is H or alkyl (1–20C) and R' is alkyl (1–20C); in addition, this group may be attached to adjacent nucleotides through O or S. Not all linkages in an oligomer need to be identical.

The nucleic acid ligands used as starting materials in the process of the invention to determine specific binding sequences may be single-stranded or double-stranded DNA or RNA. In a preferred embodiment, the sequences are single-stranded DNA. The use of DNA eliminates the need for conversion of RNA aptamers to DNA by reverse transcriptase prior to PCR amplification. Furthermore, DNA is less susceptible to nuclease degradation than RNA. In preferred embodiments, the starting nucleic acid ligand will contain a randomized sequence portion, generally including from about 10 to 400 nucleotides, more preferably 20 to 100 nucleotides. The randomized sequence is flanked by primer sequences that permit the amplification of nucleic acid ligands found to bind to the analyte. The flanking sequences may also contain other convenient features, such as restriction sites. These primer hybridization regions generally contain 10 to 30, more preferably 15 to 25, and most preferably 18 to 20, bases of known sequence.

Both the randomized portion and the primer hybridization regions of the initial oligomer population are preferably constructed using conventional solid phase techniques. Such techniques are well known in the art, such methods being described, for example, in Froehler, et al., (1986a, 1986b, 1988, 1987). Nucleic acid ligands may also be synthesized using solution phase methods such as triester synthesis, known in the art. For synthesis of the randomized regions, mixtures of nucleotides at the positions where randomization is desired are added during synthesis.

Any degree of randomization may be employed. Some positions may be randomized by mixtures of only two or three bases rather than the conventional four. Randomized positions may alternate with those that have been specified. Indeed, it is helpful if some portions of the candidate randomized sequence are in fact known.

SELEX Technology

A preferred method of selecting for nucleic acid ligand specificity involves the SELEX process. The SELEX process is described in U.S. Pat. Nos. 5,475,096, and 5,270,163, (see also WO91/19813), each incorporated by reference.

The SELEX method involves selection from a mixture of candidate nucleic acid ligands and step-wise iterations of binding, partitioning and amplification, using the same general selection scheme, to achieve virtually any desired criterion of binding affinity and selectivity. Starting from a mixture of nucleic acid ligands, preferably comprising a segment of randomized sequence, the method includes the following steps. Contacting the mixture with the target under conditions favorable for binding. Partitioning unbound nucleic acid ligands from those nucleic acid ligands that have bound specifically to target analyte. Dissociating the nucleic acid ligand-analyte complexes. Amplifying the nucleic acid ligands dissociated from the nucleic acid ligand-analyte complexes to yield mixture of nucleic acid ligands that preferentially bind to the analyte. Reiterating the steps of binding, partitioning, dissociating and amplifying through as many cycles as desired to yield highly specific, nucleic acid ligands that bind with high affinity to the target analyte.

In the SELEX process, a candidate mixture of nucleic acid ligands of differing sequence is prepared. The candidate mixture generally includes regions of fixed sequences (i.e., each of the nucleic acid ligands contains the same sequences) and regions of randomized sequences. The fixed sequence regions are selected to: (a) assist in the amplification steps; (b) mimic a sequence known to bind to the target; or (c) promote the formation of a given structural arrangement of the nucleic acid ligands. The randomized sequences may be totally randomized (i.e., the probability of finding a given base at any position being one in four) or only partially randomized (i.e., the probability of finding a given base at any location can be any level between 0 and 100 percent).

The candidate mixture is contacted with the selected analyte under conditions favorable for binding of analyte to nucleic acid ligand. The interaction between the target and the nucleic acid ligands can be considered as forming nucleic acid ligand-target pairs with those nucleic acid ligands having the highest affinity for the analyte.

The nucleic acid ligands with the highest affinity for the analyte are partitioned from those nucleic acid ligands with lesser affinity. Because only a small number of sequences (possibly only one molecule of nucleic acid ligand) corresponding to the highest affinity nucleic acid ligands exist in the mixture, it is generally desirable to set the partitioning criteria so that a significant amount of nucleic acid ligands in the mixture (approximately 5–50%) are retained during partitioning. Those nucleic acid ligands selected during partitioning as having higher affinity for the target are amplified to create a new candidate mixture that is enriched in higher affinity nucleic acid ligands.

By repeating the partitioning and amplifying steps, each round of candidate mixture contains fewer and fewer weakly binding sequences. The average degree of specificity and affinity of the nucleic acid ligands to anthrax spores will generally increase with each cycle. The SELEX process can ultimately yield a mixture containing one or a small number of nucleic acid ligands having the highest specificity and affinity for the target analyte. In different embodiments, the desired degree of specificity and binding affinity of the nucleic acid ligand(s) for anthrax spores may vary from relatively low to quite high. It is expected that at the lowest degree of specificity, the nucleic acid ligands will have a higher affinity for anthrax spores than for any other component of a sample. In preferred embodiments, the nucleic acid ligands will bind primarily to anthrax spores, with only minor binding exhibited for any other sample components. In the most preferred embodiments, the nucleic acid ligands will bind only to anthrax spores in a sample. Methods of determining specificity and binding affinity are well known in the art and may be assessed, within the scope of the present invention, by any such method.

Nucleic acid ligands produced for SELEX may be generated on a commercially available DNA synthesizer. The random region is produced by mixing equimolar amounts of each nitrogenous base (A,C,G, and T) at each position to create a large number of permutations (i.e., $4^n$, where "n" is the oligo chain length) in a very short segment. Thus a randomized 40 mer (40 bases long) would consist of $4^{30}$ or maximally $10^{24}$ different nucleic acid ligands. This provides dramatically more possibilities to find high affinity nucleic acid ligands when compared to the $10^9$ to $10^{11}$ variants of murine antibodies produced by a single mouse. The random region is flanked by two short Polymerase Chain Reaction (PCR) primer regions to enable amplification of the small subset of nucleic acid ligands that bind tightly to the target analyte.

Another advantage of DNA-based binding is that simple heating to ≧94° C. can drive off the bound analyte. Two potential technical hurdles associated with SELEX might be: 1) there are potential electrostatic repulsions between the negatively charged phosphate backbone of the nucleic acid ligands and negatively charged target molecules, but this has not been a significant problem in other recognized SELEX work, and 2) cloning, which is necessary to obtain the DNA sequence of each high affinity binding nucleic acid ligand. One final consideration is that many RNA nucleic acids have performed well due to their propensity to form secondary and tertiary structure "binding pockets", but RNAses abound in nature making RNA nucleic acids less desirable for field use. Fortunately, many single and double stranded DNA nucleic acid ligands have also demonstrated specificity and high affinity binding to their intended targets.

Nucleic Acid Chips and Aptamer Arrays

Nucleic acid chips and aptamer array technology provide a means of rapidly screening analytes for their ability to hybridize to a potentially large number of single stranded nucleic acid ligand probes immobilized on a solid substrate. In preferred embodiments, the nucleic acid ligands are DNA. Specifically contemplated are chip-based DNA technologies such as those described by Hacia et al., 1996 and Shoemaker et al., 1996. These techniques involve quantitative methods for analyzing large numbers of samples rapidly and accurately. The technology capitalizes on the binding properties of single stranded DNA to screen samples. (Pease et al., 1994; Fodor et al., 1993; Southern et al., 1994; Travis, 1997; Lipshutz et al., 1995; Matson et al., 1995; each of which is incorporated herein by reference.)

A nucleic acid ligand chip or array consists of a solid substrate upon which an array of single stranded nucleic acid ligand molecules have been attached. For screening, the chip or array is contacted with a sample containing analyte that is allowed to bind to the ligands. The degree of stringency of binding may be manipulated as desired by varying, for example, salt concentration, temperature, pH and detergent content of the medium. The chip or array is then scanned to determine which nucleic acid ligands have bound to the analyte. Prior to the present invention, DNA chips were typically used to bind to target DNA or RNA molecules in a sample.

A variety of DNA chip formats are described in the art, for example U.S. Pat. Nos. 5,861,242 and 5,578,832, incorporated herein by reference. The structure of a nucleic acid ligand chip or array comprises: (1) an excitation source; (2) an array of probes; (3) a sampling element; (4) a detector; and (5) a signal amplification/treatment system. A chip may also include a support for immobilizing the probe.

In particular embodiments, a nucleic acid ligand may be tagged or labeled with a substance that emits a detectable signal, for example, DALM. The tagged or labeled species may be fluorescent, phosphorescent, luminescent, chemiluminescent or electrochemiluminescent or it may emit Raman energy or it may absorb energy. In certain embodiments, detection may occur by enhanced chemiluminescent (ECL) detection (AP Biotech, Piscataway, N.J.). When the nucleic acid ligand binds to a targeted analyte, a signal is generated that is detected by the chip. The signal may then be processed in several ways, depending on the nature of the signal.

The nucleic acid ligand may be immobilized onto an integrated microchip that also supports a phototransducer and related detection circuitry. Alternatively, a nucleic acid ligand may be immobilized onto a membrane or filter that is then attached to the microchip or to the detector surface itself.

The nucleic acid ligands may be directly or indirectly immobilized onto a transducer detection surface to ensure optimal contact and maximum detection. The ability to directly synthesize on or attach polynucleotide probes to solid substrates is well known in the art. See U.S. Pat. Nos. 5,837,832 and 5,837,860, incorporated by reference. A variety of methods have been utilized to either permanently or removably attach the nucleic acid ligands to the substrate. Exemplary methods are described above under the section on immobilization. When immobilized onto a substrate, the nucleic acid ligands are stabilized and may be used repeatedly.

Exemplary substrates include nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane) and photopolymers which contain photoreactive species such as nitrenes, carbenes and ketyl radicals capable of forming covalent links with target molecules (U.S. Pat. Nos. 5,405,766 and 5,986,076, each incorporated herein by reference).

Binding of nucleic acid ligand to a selected support may be accomplished by any of several means. For example, DNA is commonly bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. DNA may be bound directly to membranes using ultraviolet radiation. With nitrocellulose membranes, the DNA probes are spotted onto the membranes. A UV light source (Stratalinker, from Stratagene, La Jolla, Calif.) is used to irradiate DNA spots and induce cross-linking. An alternative method for cross-linking involves baking the spotted membranes at 80° C. for two hours in vacuum. Further, it is specifically contemplated that the nucleic acid ligand may be bound to an immobilized indicator species. Therefore, in a preferred embodiment of the invention, DALM is immobilized to a solid substrate and the nucleic acid ligands attached to the immobilized DALM. Alternatively, the DALM/nucleic acid ligand complex may be bound via the DALM or the polynucleotide to the substrate.

Specific nucleic acid ligands may first be immobilized onto a membrane and then attached to a membrane in contact with a transducer detection surface. This method avoids binding the nucleic acid ligand onto the transducer and may be desirable for large-scale production. Membranes particularly suitable for this application include nitrocellulose membrane (e.g., from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

Biological Sensors and in Vivo Aptamer Production

The lac operon regulates the transcription of DNA into mRNA for translation into β-galactosidase, permease, and transacetylase. These three enzymes are necessary for the bacteria to metabolize lactose. The expression of β-galactosidase in a variety of cells including *E. coli* has become an invaluable tool for marking transfection (the insertion of foreign genes) and expression of genes. By using a medium that contains a substrate (x-gal) for β-galactosidase that turns blue upon the action of the enzyme, one can detect the insertion of foreign genes into the β-galactosidase gene. In the absence of an insert into β-galactosidase, expression of the lac operon results in a blue color on X-gal, while the presence of an insert results in a white bacterial plaque.

The lac repressor gene within the lac operon encodes a protein that prevents the enzymes in the lac operon from being expressed. The repressor protein is inactivated by binding to an inducer or de-repressor, resulting in expression of β-galactosidase and causing a blue color to form on x-gal. In the absence of an inducer or de-repressor, only the repressor is translated from the lac operon and no lactose (or color-producing substrate) metabolism occurs. The repressor gene is always translated first, before the enzymes in the operon. Therefore, if the transcription of the repressor gene is altered too much, the downstream genes will not be expressed (no blue color).

This method can be carried one step further. By inserting a marker gene in place of the β-galactosidase gene, induction or derepression of the lac operon results in the expression of the new protein in place of β-galactosidase. Other markers used to replace galactosidase include green fluorescent protein (GFP), chloramphenicol acetyltransferase (CAT), luciferase, and nitrate reductase (U.S. Pat. No. 5,902,728). The GFP makes the cells fluoresce green, CAT converts radiolabeled chloramphenicol to a more soluble product that appears in a different place on a thin-layer chromatographic plate, luciferase produces bioluminescence in transfected cells, and nitrate reductase can produce colorimetric, fluorescent, or luminescent products in cells.

A mutagen assay based on the lac operon has been incorporated into cultured animal cells and whole transgenic animals (Big Blue™ mice and rats). Mutations in the repressor gene allow for unrestricted expression of β-galactosidase and production of blue colored substrate. Thus, mutagenic activity can be assayed by measuring the level of blue plaques obtained in the absence of induction. Further, by replacing the promoter of the lac operon with another promoter that is responsive to different regulatory factors, one can test for factors that bring about expression of any gene of choice, using marker gene expression.

The problem of using the above methods is that a specific promoter must be found for each agent (regulatory factor) that is to be detected. To do this, microbes that already have the appropriate metabolic machinery to detect the presence of a specific agent must be found or genetically engineered. This has been done at Oak Ridge National Laboratory for detection of explosives using genetically engineered pseudomonads. The presence of the specific agent (explosive) induces expression of a gene encoding GFP. Thus, the pseudomonad produces GFP when spread out over ground containing landmines (leaking explosives).

It would be much more convenient to genetically engineer the lac operon of a microbe like E.coli to detect a variety of agents (analytes). By using aptamers that can be selected to bind to almost any desired target, this problem may be solved. DNA sequences comprising nucleic acid ligands may be incorporated into the repressor gene or its promoter in such a way that when the target analyte binds to the nucleic acid ligand, expression of the repressor protein is inhibited and β-galactosidase or another marker gene is expressed. Thus, blue colonies or other markers will appear in the presence of the designed inducer (i.e. the target analyte). Since aptamers with high affinity against virtually any target analyte can be prepared and sequenced using the methods described herein, it would be possible to design an appropriate biosensor microorganism that is capable of detecting almost any molecule in the environment.

It is envisioned within the scope of the invention that the target analyte could bind to the nucleic acid ligand either within the intact repressor gene or its promoter, or in the mRNA transcript of the repressor gene, prior to its translation into protein. High-affinity binding of analyte to mRNA would interfere with ribosomal binding and mRNA translation. For this reason, in preferred embodiments it may be desirable for the ligand insertion site to be close to the ribosomal binding site of the repressor gene sequence, allowing for steric hindrance of ribosomal binding.

This process can be extended to a large library of aptamers, each of which is inserted into the same site of the repressor gene or its promoter. The process can thus be used to select an appropriate nucleic acid ligand for a target analyte of choice by selecting for a bacterial clone that is colored blue or otherwise marked only in the presence of the target analyte. Amplification of the selected clone and DNA sequencing would result in the identification of aptamer sequences that can bind with high affinity to the target analyte. The normal inducer will also work because it acts on the repressor gene product (the repressor protein itself) rather than the machinery to translate the gene into protein (like the aptamer). This is an important positive control to confirm the fidelity of the system. This method would allow for screening of nucleic acid ligand libraries and selection and amplification of nucleic acid ligands with high affinity for a target analyte, as an alternative to the SELEX process. Purified nucleic acid ligands of appropriate binding specificity may be obtained either by chemical synthesis or by PCR or other amplification processes using primers selected to flank the ligand insertion site.

The process may also be adapted for use with a recognition complex system. By cloning in E. coli (see U.S. Pat. No. 5,902,728, incorporated herein by reference) or another appropriate host that has been genetically engineered to produce the organic semiconductor, such as DALM, then growth on an appropriate medium will result in the production of aptamers that are already operatively linked to the organic semiconductor.

Formulations and Routes for Administration to Patients

Where clinical applications are contemplated, it will be necessary to prepare pharmaceutical compositions—such as therapeutic nucleic acid ligands—in a form appropriate for the intended application. Generally, this will entail preparing compositions that are essentially free of pyrogens, as well as other impurities that could be harmful to humans or animals.

Aqueous compositions of the present invention comprise an effective amount of the ligand to cells, dissolved or dispersed in a pharmaceutically acceptable carrier or aqueous medium. Such compositions also are referred to as innocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the nucleic acid ligands of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions normally would be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically-acceptable salts include the acid addition salts which are formed by reaction of basic groups with inorganic acids such as, for example, hydrochloric or phosphoric acids, or such organic acids as acetic, oxalic, tartaric, mandelic, and the like. Salts formed with free acidic groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In Vitro Selection of High Affinity Nucleic Acid Ligands for Anthrax Spores Functional nucleic acid ligands can be selected from random-sequence nucleic acid pools by a process known as SELEX. This technique allows repetitive cycles of selection and amplification of single-stranded nucleic acids in vitro (Tuerk and Gold, 1990; Ellington and Szostak, 1990). SELEX methodology was used to develop high affinity single stranded DNA (ssDNA) ligands that bind to live anthrax spores. The mixture of ssDNA and target (anthrax spores) was allowed to interact. Nucleic acid ligands that bound to the spores were separated from unbound ligands using a nitrocellulose filter method. Aptamers that bound to anthrax spores were separated from the spores and used for the next round of selection.

Libraries and Primers: The starting material for SELEX preparation of anti-anthrax spores comprised synthetic DNA containing fixed sequences for primer annealing in a PCR amplification reaction. The starting nucleic acid ligand library was composed of 86-mers, containing 40-mer random DNA sequences (N40) attached to 5' and 3' fixed primer annealing sequences, as shown in Table 2 below.

TABLE 2

| 5' Fixed sequences for primer annealing | Random sequences | 3' Fixed sequences for primer annealing |
|---|---|---|
| 5'-CCCCTGCAGGTGATTTT GCTCAAGT-3' (SEQ ID NO: 1) | NNNN - - - NNNN (40N) | 5'-AGTATCGCTAATCA GGCGGAT-3' (SEQ ID NO: 2) |

In the Table above, N represents an equal mixture of all four nucleotides (A, G, T and C). The 5' end of the 5' fixed sequence was covalently attached to three biotin residues to facilitate binding of the nucleic acid ligands to streptavidin. The oligonucleotide library and corresponding PCR primers were purchased from Genosys (The Woodland, Tex.). Taq polymerase was obtained from Display Systems Biotech (Vista, Calif.). A dNTP mixture was purchased from Applied Biosystems (Foster City, Calif.). Ultra pure urea, bis-acrylamide, fluor-coated TLC plates and buffer saturated phenol were from Ambion (Austin, Tex.). Glycogen and streptavidin-linked beads were purchased from Roche Molecular Biochemicals (Indianapolis, Ind.). Spin columns and 10×TBE (Tris-borate-EDTA) buffer were from BioRad (Hercules, Calif.). Nitrocellulose discs were from Millipore (Bedford, Mass.). All other reagent grade chemicals were purchased from Sigma (St. Louis, Mo.). Anthrax Spore Vaccine, a non-encapsulated live culture, was supplied by the Colorado Serum Company (Denver, Colo.).

Anthrax Spores: Anthrax spore vaccine was transferred from the manufacturer's vial to sterile centrifugation tubes that had been chilled on ice. The spores were pelleted by centrifuging at 9500×g for 10 min at 4° C. and the pellet was washed with ice cold sterile distilled water. Spores were resuspended in ice cold, sterile distilled water and stored temporarily at 4° C.

AK sporulation agar was used to make agar plates according to the manufacturer's instructions. Sterile cotton-tipped swabs were used to streak each agar plate with the anthrax spore suspension. Plates were incubated at 37° C. for 4 days and then checked for complete sporulation under a light microscope. Spores were harvested from the plates by using sterile cotton tipped swabs wetted with distilled water. The swab was run across the plate and placed into sterile ice-cold distilled water. The entire layer of anthrax growth was removed and transferred to distilled water. The spore suspension was then vacuum filtered using a sterile Buchner funnel and Whatman filter paper into a sterile flask in an ice bath. The spores are filtered through the filter paper while vegetative debris is trapped on the filter paper. The filtrate consisted almost entirely of spores. The spores were heat treated at 65° C. for 30 min and cooled immediately in an ice bath. The suspension was centrifuged at 9500×g for 10 min, resuspended in ice cold sterile distilled water and stored at 4° C. until use. Stock spore suspension concentration was determined from the average colony forming units (CFUs) obtained from triple replicates at five different dilutions of stock suspension.

The initial nucleic acid ligand library was amplified by PCR. The 5' primer used was identical to SEQ ID NO:1, disclosed above, with 3 biotin residues attached to the 5' end of the primer. The 3' primer was complementary to the 3' fixed sequence disclosed in Table 2 and is shown below as SEQ ID NO:3. PCR conditions were checked in 200 µL reaction mixture, using 5 pmol of template and 0.1 µM of each primer, 20 µL of 10×PCR reaction buffer, 2 µL of 10 mM dNTP mix and 5 units of display TAQ polymerase, with distilled water added to 200 µL. Optimal PCR conditions were determined to be denaturation at 94° C. for 3 min, annealing at 45° C. for 30 sec, and extension at 72° C. for 1 min, with a final extension at 72° C. for 3 min. The reaction was performed using a Robocycler Model 96 thermal cycler with a "Hot Top" assembly (Stratagene, La Jolla, Calif.). The PCR product was checked every third cycle and the optimal number of cycles determined. After obtaining optimal conditions, the original library was amplified to prepare 25 ml of reaction mix (125 reactions at 200 µL each). The amplified DNA pool was recovered by ethanol precipitation in the presence of glycogen and the final DNA pellet was resuspended in sterile TE buffer [Tris-HCl, EDTA, pH 8.0] and used for streptavidin binding.

5'-ATCCGCCTGATTAGCGATACT-3' (SEQ ID NO:3)

Streptavidin Binding: Resuspended double stranded DNA was mixed with streptavidin agarose beads and incubated at room temperature to allow binding of biotin labeled DNA to streptavidin. The mixture was transferred to spin columns and denatured by addition of 0.2 M NaOH. The biotin labeled DNA strand remained in the column along with the streptavidin beads, while the unlabeled strand passed through the column and was collected. The eluate was neutralized with 3 M sodium acetate, pH 5.0, ethanol precipitated overnight and recovered by centrifugation at 4° C. at 13,000 rpm. The ssDNA pellet was resuspended in TE buffer and used for gel purification.

Gel Purification of ssDNA: The ssDNA was mixed with a denaturing 2×sample buffer containing 90% formamide, 1 mM EDTA and 0.1% bromophenol blue and heated at 90° C. for 5 min. After cooling to room temperature, the contents were separated by electrophoresis in a 6% acrylamide/bis (19:1) gel, with 7M urea in 1×TBE buffer for 2 hours at 150 volts. The ssDNA was visualized under UV light and the bands cut out and eluted overnight in 0.3 M sodium chloride. Eluted DNA was ethanol precipitated overnight and collected by centrifugation. The DNA pellet was resuspended in TE buffer and used for in vitro selection.

In vitro Selection by SELEX: To exclude filter-binding ssDNA sequences from the pool, the DNA was initially passed over a 0.45 µm HAWP filter (Millipore, Bedford, Mass.) and washed with TE buffer. The filtrate containing non-binding DNA was used for in vitro selection. In general, the final yield of ssDNA was in the µmole range. One hundred pmol of ssDNA was incubated with live anthrax spores (0.5×10⁶ spores) in binding buffer (20 mM Tris-HCl, pH 7.5, 45 mM sodium chloride, 3 mM magnesium chloride, 1 mM EDTA, 1 mM diothiothreitol in a final volume of 250 µL) according to Hesselberth et al. (2000). The binding reaction mixture was incubated for one hour at room temperature, then vacuum filtered through a HAWP filter at 5 psi and washed twice with 0.2 ml of binding buffer. DNA that bound to anthrax spores was retained on the filter, while nucleic acid ligands that did not bind to anthrax passed through the filter. The anthrax-binding ssDNA was eluted 2× with 0.2 ml of 7 M urea, 100 mM MES (4-morpholine-ethansulfonic acid, Roche Molecular Biochemicals), pH 5.5, 3 mM EDTA for 5 min at 100° C. The eluted anthrax-binding ssDNA was ethanol precipitated overnight and collected by centrifugation. The pelleted DNA was resuspended and used for the next round of SELEX selection.

Results: The methods described above resulted in the production of ssDNA nucleic acid ligands that bind with high affinity to live anthrax spores (*Bacillus anthracis* Sterne strain). In vitro selection was performed using the SELEX procedure as described above. (Robertson and Joyce, 1990; Tuerk and Gold, 1990; Ellington and Szostak, 1990). Nucleic acid ligands containing 40 bp random DNA sequences were screened for binding to live anthrax spores. Anthrax-binding nucleic acid ligands were eluted, amplified by PCR and subjected to further rounds of SELEX screening. A total of seven rounds of SELEX screening were performed. Gel electrophoresis analysis showed that the PCR amplification products after each round were the same size (86-mer) as the original pool, demonstrating that the primers were amplifying nucleic acid ligand sequences, not anthrax genomic sequences. Controls performed in the absence of anthrax spores, or in the presence of spores but the absence of the ssDNA pool, showed no PCR amplification product, demonstrating that the SELEX procedure resulted in the production of anthrax-binding nucleic acid ligands.

Figure 4:
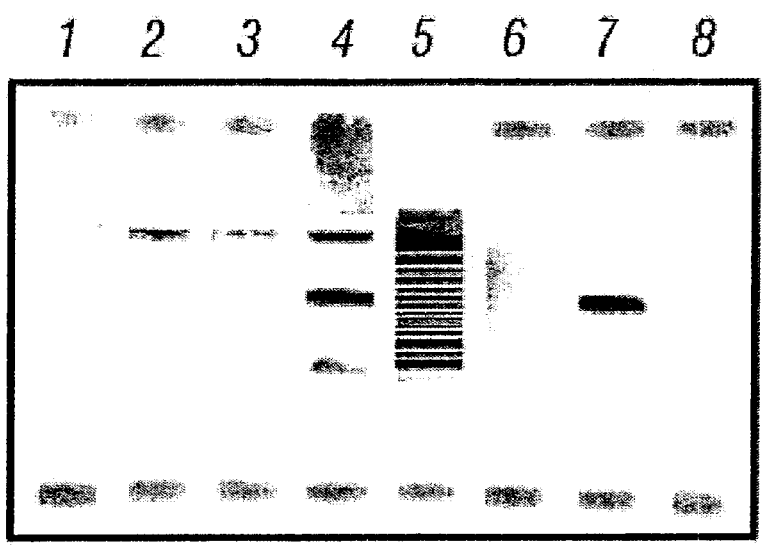
FIG. 4 illustrates a PCR amplified product from an anti-anthrax aptamer after ten cycles of selection.

FIG. 4 shows a representative gel electrophoresis analysis of anthrax-binding nucleic acid ligands after five rounds of SELEX selection (FIG. 4, lane 4). The amplification product (after 10 PCR cycles) is present as essentially a single band. A zero amplification control (FIG. 4, lane 3) shows that the band is not observed in the absence of amplification. A positive PCR control (FIG. 4, lane 7) shows that the anthrax-binding amplification product is the same size as the PCR amplification products of the initial random nucleic acid library. The positive control was run on the gel after seven cycles of PCR amplification.

The sequences of anthrax-binding nucleic acid ligands identified by the disclosed methods were as shown below.

SEQ ID NO:4
5'-GGATGAAATTATGAAGGAGTAATAGTGTGATGG AGTGGTA-3'

SEQ ID NO:5
5'-ACCCGGTTAATTCGTAGTAGAGGAGGGTCGTTT GGAGTCA-3'

SEQ ID NO:6
5'-AGAGGAATGTATAAGGATGTTCCGGGCGTGTGG GTAAGTC-3'

Example 2

Neutralization of Anthrax Spores Using DALM

In a preferred embodiment of the instant invention, nucleic acid ligands with high affinity for anthrax spores are produced and purified using the disclosed methods. Such nucleic acid ligands may be used to neutralize biohazardous agents, such as viruses, microbes, spores or potentially single molecules. More preferably, high-affinity nucleic acid ligands against anthrax may be used to neutralize anthrax spores in the field.

High affinity nucleic acid ligands may be produced as disclosed in the preceding example. Such nucleic acid ligands may be attached to a compound such as DALM. The nucleic acid ligand provides specificity of binding to the target. The DALM-nucleic acid ligand couplet is then used essentially as a photochemical transducer.

DALM is capable of absorbing electromagnetic radiation within a broad range of wavelengths and transmitting the absorbed energy to molecules or targets to which it is attached. DALM attached to a target via a bound nucleic acid ligand is irradiated with a pulse of electromagnetic radiation. The radiation may be transmitted in the form of visible light or infrared radiation, but other forms of irradiation, such as microwave, laser or radio-frequency are contemplated within the scope of the present invention. Irradiation results in absorption of energy by DALM, which is transmitted to the target. The resulting heating and production of reactive chemical species produces an explosive surface reaction that destroys the target.

DALM activated by hydrogen peroxide and bicarbonate and pulsed with microwave radiation acts as a photochemical transducer, releasing an intense pulse of visible light (not shown). High power pulsed microwave radiation (HPM), applied to solutions containing dissolved carbon dioxide (or bicarbonate), hydrogen peroxide and DALM generates sound, pulsed luminescence and electrical discharge. Microbes exposed to these conditions experience damage comparable to short time, high temperature insults, even though measurable localized temperatures were insufficient to cause the observed effects.

Anthrax Spores: Sterne strain veterinary vaccine anthrax spores (Thraxol-2, Mobay Corp., Shawnee, Kans.) were streaked onto blood agar plates and incubated at 37° C. for 5 days to promote extensive sporulation and autolysis of vegetative cells. Colonies were gently washed and scraped from blood agar plates into 10 ml of filter-sterilized deionized water. The resultant suspension consisted almost exclusively of spores. Vegetative cell debris appeared to be largely removed by three washes in 10 ml of filter-sterilized deionized water with resuspension and centrifugation at 9,300×G for 10 min, as determined by phase-contrast microscopy. Stock spore suspension concentration was determined by the average of four hemocytometer counts to be $6.5 \times 10^6$ spores/ml (standard deviation=$0.24 \times 10^6$) using phase-contrast microscopy at 600×magnification.

DALM Mediated Neutralization of Anthrax Spores: *Bacillus anthracis* spores were incubated with DALM and exposed to a high power microwave (HPM) pulse. *Bacillus anthracis* (Sterne strain) spore vaccine (Thraxol™, Mobay Corp., Animal Health Division, Shawnee, Kans.) was centrifuged, the supernatant decanted and the button washed with chilled deionized water. Dilute powdered milk solution was made to a concentration of 25 mg of powdered milk solids/ml of deionized water, filtered through a 0.2 micron filter. The anthrax pellet was resuspended in 1 ml of sterile milk solution to form an anthrax spore suspension.

For pulsed microwave exposure, 0.5 ml of anthrax spore suspension was placed into 0.2 micron-filter centrifuge tubes (Microfilterfuge™, Rainin Instrument Co., Inc., Woburn, Mass.). The spores were centrifuged onto the filter at 16,000×g for 15 min. The tubes were refilled with 1.5 ml of a reaction mixture consisting of 0.9 ml saturated sodium bicarbonate/luminol solution, 0.1 ml of 1:10 biosynthetic DALM, 0.6 ml of 1:10 diazoluminol, and 0.33 ml 3% hydrogen peroxide. All dilutions were made in saturated sodium bicarbonate/luminol solution. The final dilution of DALM was 1:1000. A detailed description of the reaction mixture has been published (Kiel et al., 1999a; Kiel et al., 1999b).

The filter, with the anthrax spores, was inserted into the tube to a level just below the meniscus of the fluid. The solution was exposed to 10 pulses per second of HPM (1.25 GHz, 6 μsec pulse, 2 MW peak incident power), starting at 3 minutes and 22 seconds after placing the reaction mixture in front of the microwave waveguide. The exposure lasted for 13 min and 28 sec. Total radiation exposure was for 48 msec. The temperature of the sample, continuously monitored with a non-perturbing, high-resistance temperature probe (Vitek™), began at 25.3° C. and reached an end point of 64° C., below the lethal temperature for anthrax spores.

Figure 5A:
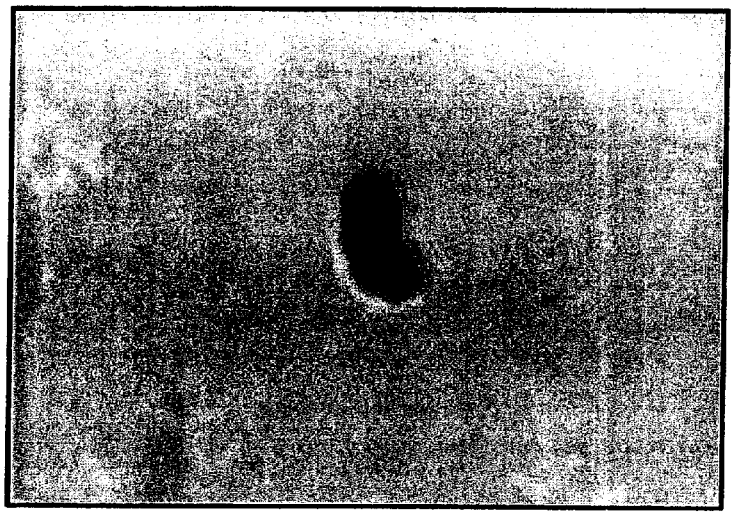
FIG. 5A–FIG. 5B show the destruction of an anthrax spore using DALM and a high power microwave pulse.
Figure 5B:

Results: FIGS. 5A–5B shows the result of this procedure. The control spore (FIG. 5A) was exposed to HPM in the absence of DALM. It remained intact. The anthrax spore shown in FIG. 5B was exposed to HPM in the presence of DALM. The spore lysed, with its contents spread around the remnants of the spore (FIG. 5B). The effect of HPM and DALM on anthrax spores shows that DALM coupled to nucleic acid ligands may be used to neutralize biohazardous agents, such as anthrax, against which high affinity nucleic acid ligands are prepared by the methods disclosed herein.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Betz et al., *Cytometry* 5: 145–150, 1984.
Bruno and Yu, Immunomagnetic-electrochemiluminescent detection of *Bacillus anthracis* spores in soil matrices. *Appl. Environ. Microbiol.* 62: 3474–76, 1996.
Effenhauser, et al *Anal. Chem.*, 66:2949–2953, 1994.
Effenhauser, et al. *Anal. Chem.*, 65:2637–2642, 1993.
Egholm et al., *Nature,* 365:566, 1993.
Ellington and Szostak, In vitro selection of RNA molecules that bind specific ligands. *Nature* 346: 818–822, 1990.
Fodor et al., Multiplexed biochemical assays with biological chips. *Nature* 364, 555–556, 1993
Freifelder, *Physical Biochemistry Applications to Biochemistry and Molecular Biology,* 2nd ed. Wm. Freeman and Co., New York, N.Y., 1982.
Frengen et al., *Clin. Chem.* 40/3: 420425, 1994.
Froehler, B., *Tet Lett.* 27:5575–5578, 1986a.
Froehler, B., et al., *Nucleic Acids Research,* 14:5399–5467, 1986b.
Froehler, B., et al. *Nucleosides and Nucleotides,* 6:287–291, 1987.

Froehler, B., et al. *Nucleic Acids Research*, 16:4831–4839, 1988.
Frohman, In: *PCR™ Protocols: A Guide To Methods And Applications*, Academic Press, N.Y., 1990.
Gatto-Menking et al., Sensitive detection of biotoxoids and bacterial spores using an immunomagnetic electrochemiluminescence sensor. *Biosensors Bioelectronics* 10: 501–507, 1995.
Griffith et al., *Cytometry* 25: 133–143, 1996.
Hacia et al., *Nature Genetics*, 14:441–447, 1996
Harrison et al., *Science*, 261:895–897, 1993.
Holmstrom, K. et al., *Anal. Biochem.* 209:278–283, 1993.
Innis et al., *PCR Protocols*, Academic Press, Inc., San Diego Calif., 1990.
Jacobson, et al., *Anal. Chem.*, 66:1107–1113, 1994.
Jayasena, S. D., Aptamers: An Emerging Class of Molecules That Rival Antibodies in Diagnostics. *Clin. Chem.* 45: 1628–1650, 1999.
Kiel et al. "Luminescent radio frequency radiation dosimetry." *Bioelectromagnetics* 20:46–51, 1999a.
Kiel et al., "Pulsed microwave induced light, sound, and electrical discharge enhanced by a biopolymer." *Bioelectromagnetics* 20:216–223, 1999b.
Klug and Famulok, All you wanted to know about SELEX. *Mol. Biol. Reports* 20: 97–107, 1994.
Kwoh et al., *Proc. Nat. Acad. Sci. USA*, 86: 1173, 1989.
Kugler et al., "Photoelectron spectroscopy and quantum chemical modeling applied to polymer surfaces and interfaces in light-emitting devices." *Accounts of Chemical Research* 32:225–234, 1999.
Lipshutz et al., Using oligonucleotide probe arrays to access genetic diversity. *Biotechniques* 19: 442–447, 1995.
Lorsch and Szostak, In vitro selection of nucleic acid sequences that bind small molecules. In: *Combinatorial Libraries: Synthesis, Screening and Application Potential.* (R. Cortese, ed.) Walter de Gruyter Publishing Co., New York, pp. 69–86, 1996.
Manz, et al., *J. Chromatogr.*, 593:253–258, 1992.
Matson et al., Biopolymer synthesis on polypropylene supports: oligonucleotide arrays. *Anal. Biochem.* 224: 110–116, 1995.
Newton, et al. *Nucl. Acids Res.* 21:1155–1162, 1993.
Ohara et al., *Proc. Nat'l Acad. Sci. USA*, 86:5673–5677, 1989.
Pease et al., Light-generated oligonucleotide arrays for rapid DNA sequence analysis. *Proc. Natl. Acad. Sci. USA* 91: 5022–26, 1994.
Rasmussen, et al., *Anal. Biochem*, 198:138–142, 1991.
Reif et al., Identification of capsule-forming *Bacillus anthracis* spores with the PCR and a novel dual-probe hybridization format. *Appl. Environ. Microbiol.* 60:1622–25, 1994.
Robertson and Joyce, *Nature* 344:467–468, 1990.
Running. J. A. et al., *BioTechniques* 8:276–277, 1990.
Sambrook et al., In. *Molecular Cloning: A Laboratory Manual*, 2d Ed., Cold Spring Harbor Laboratory Press, Cold Spring Harbor, N.Y., 1989.
Scheit, Nucleotide Analogs, John Wiley, New York, 1980
Scillian et al., *Blood* 73: 2041–2048, 1989.
Shoemaker et al., *Nature Genetics* 14:450–456, 1996.
Southern et al., Arrays of complementary oligonucleotides for analyzing the hybridization behaviour of nucleic acids. *Nucleic Acids Res.* 22: 1368–73, 1994.
Stuart et al., *Cytometry* 33: 414–419, 1998.
Travis, Chips ahoy: microchips covered with DNA emerge as powerful research tools. *Science News* 151:144–45, 1997.
Tsuda et al., *Anal. Chem.*, 62:2149–2152, 1990.
Tuerk, In vitro evolution of functional nucleic acids: high-affinity RNA ligands of HIV-1 proteins. *Gene* 137: 33–39, 1993.
Tuerk, Using the SELEX combinatorial chemistry process to find high affinity nucleic acid ligands to target molecules. *Meth. Mol. Biol.* 67: 219–30, 1997.
Tuerk and Gold, Systematic evolution of ligands by exponential enrichment: RNA ligands to bacteriophage T4 DNA polymerase. *Science* 249: 505–510, 1990.
Walker et al., *Proc. Natl. Acad. Sci. USA,* 89:392–396 1992.
Weetall, H. W. in: *Methods in Enzymology,* K. Mosbach (ed.), 44:134–148, 140, 1976
Wilson et al., *J. Immunol. Methods* 107: 231–237, 1988.
Woolley and Mathies, *Proc Natl Acad Sci USA*, 91:11348–52, 1994.
Wu et al., *Genomics,* 4:560, 1989.
U.S. Pat. No. 09/608,706
U.S. Pat. No. 3,652,761
U.S. Pat. No. 3,970,518
U.S. Pat. No. 3,933,997
U.S. Pat. No. 4,230,685
U.S. Pat. No. 4,267,234
U.S. Pat. No. 4,599,307
U.S. Pat. No. 4,677,055
U.S. Pat. No. 4,683,195
U.S. Pat. No. 4,683,202
U.S. Pat. No. 4,695,393
U.S. Pat. No. 4,704,891
U.S. Pat. No. 4,727,020
U.S. Pat. No. 4,800,159
U.S. Pat. No. 4,883,750
U.S. Pat. No. 5,003,050
U.S. Pat. No. 5,270,163
U.S. Pat. No. 5,405,766
U.S. Pat. No. 5,475,096
U.S. Pat. No. 5,539,082
U.S. Pat. No. 5,567,588
U.S. Pat. No. 5,578,832
U.S. Pat. No. 5,580,737
U.S. Pat. No. 5,595,877
U.S. Pat. No. 5,610,287
U.S. Pat. No. 5,637,459
U.S. Pat. No. 5,641,629
U.S. Pat. No. 5,645,897
U.S. Pat. No. 5,650,275
U.S. Pat. No. 5,670,637
U.S. Pat. No. 5,683,867
U.S. Pat. No. 5,696,249
U.S. Pat. No. 5,705,629
U.S. Pat. No. 5,707,796
U.S. Pat. No. 5,714,331
U.S. Pat. No. 5,719,262
U.S. Pat. No. 5,736,336
U.S. Pat. No. 5,763,177
U.S. Pat. No. 5,766,855
U.S. Pat. No. 5,773,571
U.S. Pat. No. 5,786,461
U.S. Pat. No. 5,789,157
U.S. Pat. No. 5,817,785
U.S. Pat. No. 5,837,832
U.S. Pat. No. 5,837,860
U.S. Pat. No. 5,843,653
U.S. Pat. No. , 5,853,984
U.S. Pat. No. 5,856,108
U.S. Pat. No. 5,856,174
U.S. Pat. No. 5,861,242

| U.S. Pat. No. 5,864,026 | U.S. Pat. No. 6,303,316 |
| U.S. Pat. No. 5,874,218 | EPO App. No. 266,032 |
| U.S. Pat. No. 5,891,625 | EPO App. No. 320,308 |
| U.S. Pat. No. 5,904,824 | EPO App. No. 329,822 |
| U.S. Pat. No. 5,908,845 | PCT/EP/01219 |
| U.S. Pat. No. 5,948,627 | PCT App. No. US 87/00880 |
| U.S. Pat. No. 5,958,691 | PCT App. No. US 89/01025 |
| U.S. Pat. No. 5,972,721 | PCT App. No. WO 88/10315 |
| U.S. Pat. No. 5,986,076 | PCT App. No. WO 89/06700 |
| U.S. Pat. No. 5,989,823 | PCT App. No. WO 91/19813 |
| U.S. Pat. No. 6,001,577 | PCT App. No. WO 92/20702 |
| U.S. Pat. No. 6,030,776 | PCT App. No. WO 99/31275 |

What is claimed is:

1. A composition comprising one or more anthrax-binding nucleic acid ligands.

2. The composition of claim 1, wherein the one or more ligands bind to anthrax spores with high affinity.

3. The composition of claim 1, wherein the one or more ligands bind specifically to anthrax spores.

4. The composition of claim 1, wherein the one or more ligands comprise the sequence of SEQ ID NO:4, SEQ ID NO:5 or SEQ ID NO:6.

5. An isolated nucleic acid comprising at least six contiguous nucleotides having a sequence selected from the group consisting of SEQ ID NO:4, SEQ ID NO:5 and SEQ ID NO:6.

6. The isolated nucleic acid of claim 5, further comprising at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 contiguous nucleotides having a sequence selected from SEQ ID NO:4.

7. The isolated nucleic acid of claim 5, further comprising at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 contiguous nucleotides having a sequence selected from SEQ ID NO:5.

8. The isolated nucleic acid of claim 5, further comprising at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 contiguous nucleotides having a sequence selected from SEQ ID NO:6.

9. A composition comprising an isolated nucleic acid according to claim 5.

10. The composition of claim 9, wherein said isolated nucleic acid is incorporated into a vector.

11. The composition of claim 10, wherein said vector is a plasmid, virus, phage, cosmid, YAC or BAC.

12. The isolated nucleic acid of claim 5, wherein said isolated nucleic acid is attached to an organic semiconductor.

13. The isolated nucleic acid of claim 12, wherein said organic semiconductor is DALM.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic Oligonucleotide

<400> SEQUENCE: 1
cccctgcagg tgattttgct caagt                                          25

<210> SEQ ID NO 2
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic Oligonucleotide

<400> SEQUENCE: 2
agtatcgcta atcaggcgga t                                              21

<210> SEQ ID NO 3
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic Oligonucleotide

<400> SEQUENCE: 3
atccgcctga ttagcgatac t                                              21

<210> SEQ ID NO 4
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic Oligonucleotide

<400> SEQUENCE: 4
ggatgaaatt atgaaggagt aatagtgtga tggagtggta                          40

<210> SEQ ID NO 5
<211> LENGTH: 40

```
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic Oligonucleotide

<400> SEQUENCE: 5
acccggttaa ttcgtagtag aggagggtcg tttggagtca                              40

<210> SEQ ID NO 6
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic Oligonucleotide

<400> SEQUENCE: 6
agaggaatgt ataaggatgt tccgggcgtg tgggtaagtc                              40
```